(12) United States Patent
Kobayashi

(10) Patent No.: US 10,543,159 B2
(45) Date of Patent: Jan. 28, 2020

(54) HAIR PAPILLA CELL ACTIVATOR

(71) Applicant: Ezaki Glico Co., Ltd., Osaka-shi, Osaka (JP)

(72) Inventor: Takatsugu Kobayashi, Osaka (JP)

(73) Assignee: EZAKI GLICO CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 15/528,454

(22) PCT Filed: Sep. 1, 2015

(86) PCT No.: PCT/JP2015/004439
§ 371 (c)(1),
(2) Date: May 19, 2017

(87) PCT Pub. No.: WO2016/079912
PCT Pub. Date: May 26, 2016

(65) Prior Publication Data
US 2017/0312208 A1 Nov. 2, 2017

(30) Foreign Application Priority Data
Nov. 20, 2014 (JP) .................. 2014-235352

(51) Int. Cl.
*A61K 8/60* (2006.01)
*A61Q 7/00* (2006.01)
*A61K 8/19* (2006.01)

(52) U.S. Cl.
CPC ............ *A61K 8/60* (2013.01); *A61K 8/19* (2013.01); *A61K 8/606* (2013.01); *A61Q 7/00* (2013.01)

(58) Field of Classification Search
None
See application file for complete search history.

(56) References Cited

U.S. PATENT DOCUMENTS

| | | | |
|---|---|---|---|
| 2,856,327 A * | 10/1958 | Shaw ................ | A61K 31/70 514/53 |
| 5,861,048 A | 1/1999 | Kamasaka et al. | |
| 6,268,182 B1 | 7/2001 | Kamasaka et al. | |
| 7,678,368 B2 | 3/2010 | Mizutani et al. | |
| 2002/0035070 A1 | 3/2002 | Gardlik et al. | |
| 2008/0274068 A1 | 11/2008 | Tanaka et al. | |
| 2014/0023602 A1 | 1/2014 | Tanaka et al. | |

FOREIGN PATENT DOCUMENTS

| | | | |
|---|---|---|---|
| JP | 63-150210 A | 6/1988 | |
| JP | 1-163114 A | 6/1989 | |
| JP | 4-187622 A | 7/1992 | |
| JP | 5-117131 A | 5/1993 | |
| JP | 8-104696 A | 4/1996 | |
| JP | 9-188607 A | 7/1997 | |
| JP | 10-203930 A | 8/1998 | |
| JP | 11-158197 A | 6/1999 | |
| JP | 2000-198719 A | 7/2000 | |
| JP | 2003-183133 A | 7/2003 | |
| JP | 2004-238286 A | 8/2004 | |
| JP | 2006-249077 A | 9/2006 | |
| JP | 3831252 B2 | 10/2006 | |
| JP | 2012-77044 A | 4/2012 | |
| WO | WO-0207685 A2 * | 1/2002 | ............... A61K 8/19 |
| WO | 2007/086327 A1 | 2/2007 | |
| WO | 2007/040027 A1 | 4/2007 | |
| WO | WO-2013160349 A2 * | 10/2013 | ............... A61K 8/60 |

OTHER PUBLICATIONS

Azam, Aloe vera, Properties and Value added Products, Central Arid Zone Research Institute, 2011. (Year: 2011).*
Ikeda, JP 2007238444 A, Sep. 20, 2007, abstract only. (Year: 2007).*
Extended European Search Report, dated May 18, 2018, for European Application No. 15861022.0-1112 / 3222269, 8 pages.
English translation of International Search Report, dated Oct. 20, 2015, for corresponding international application No. PCT/JP2015/004439, 4 pages.
Romanowska et al., "Wnt5a Exhibits Layer-Specific Expression in Adult Skin, Is Upregulated in Psoriasis, and Synergizes with Type 1 Interferon," *PLoS One* 4(4):e5354, Apr. 2009, 10 pages.
Soma et al., "Hair cycle-specific expression of versican in human hair follicles," *Journal of Dermatological Science* 39:147-154, 2005.
Xing et al., "Immunolocalization of Wnt5a during the hair cycle and its role in hair shaft growth in mice," *Acta Histochemica* 113:608-612, 2011.

* cited by examiner

*Primary Examiner* — Layla D Berry
(74) *Attorney, Agent, or Firm* — Seed IP Law Group LLP

(57) ABSTRACT

The present invention provides an agent for activating proliferation of follicle dermal papilla cells comprising an acidic saccharide alkaline earth metal salt, wherein the acidic saccharide is selected from the group consisting of a phosphorylated saccharide and lactobionic acid. The acidic saccharide is preferably a phosphorylated saccharide. The alkaline earth metal salt is preferably a calcium salt or a magnesium salt. In accordance with the present invention, the proliferation of follicle dermal papilla cells is promoted. Thus, the agent for activating proliferation of follicle dermal papilla cells is expected to produce hair-restoration and hair-growth effects such as treatment of hair thinning, prevention of hair loss, promotion of hair restoration, and promotion of hair growth.

10 Claims, 8 Drawing Sheets
Specification includes a Sequence Listing.

n=4, t-test, bar: $p<0.05$ n=4, t-test, bar: $p<0.05$

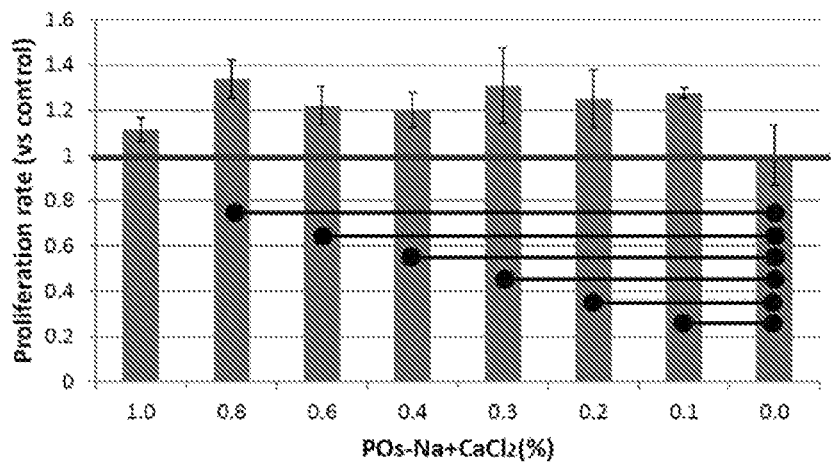
Fig. 1D  POs-Na + CaCl₂ HFDPC proliferation
n=4, t-test, bar: p<0.05
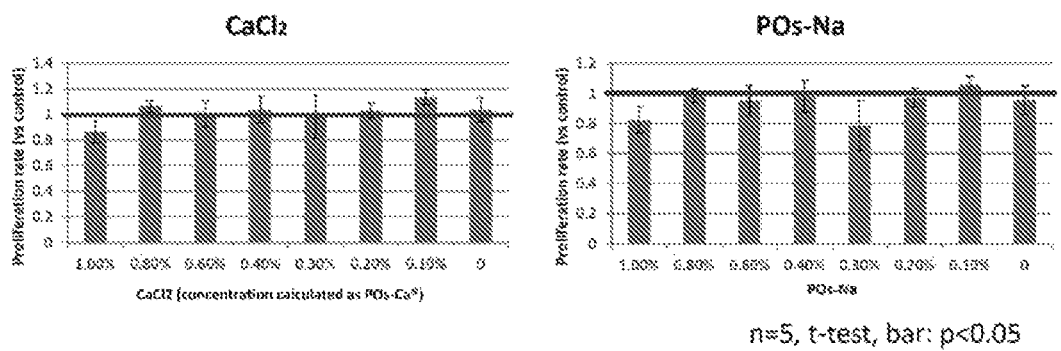
Fig. 1E
n=5, t-test, bar: p<0.05

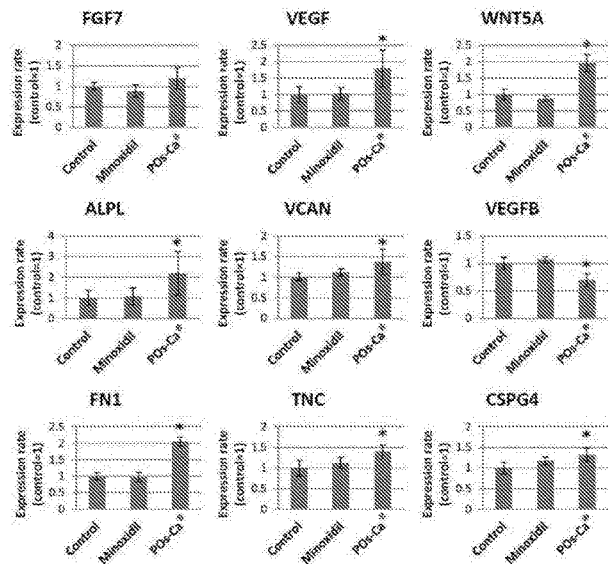

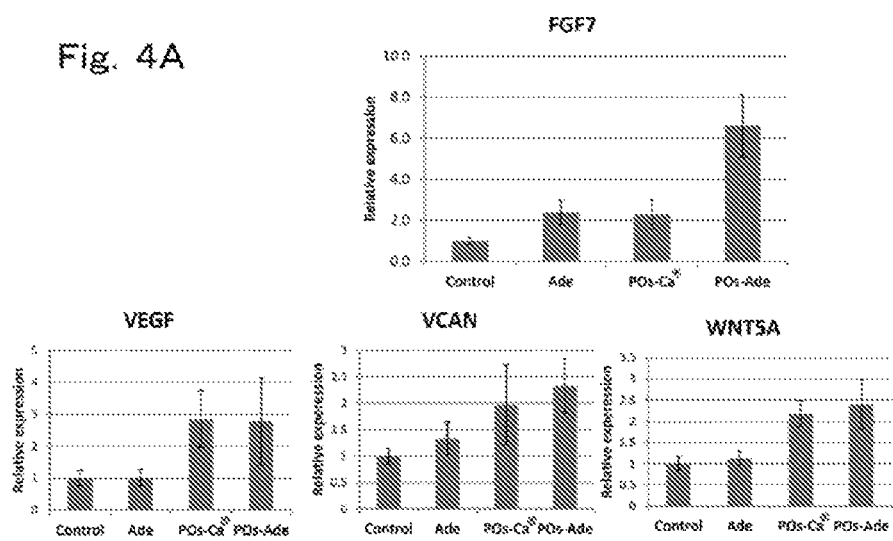
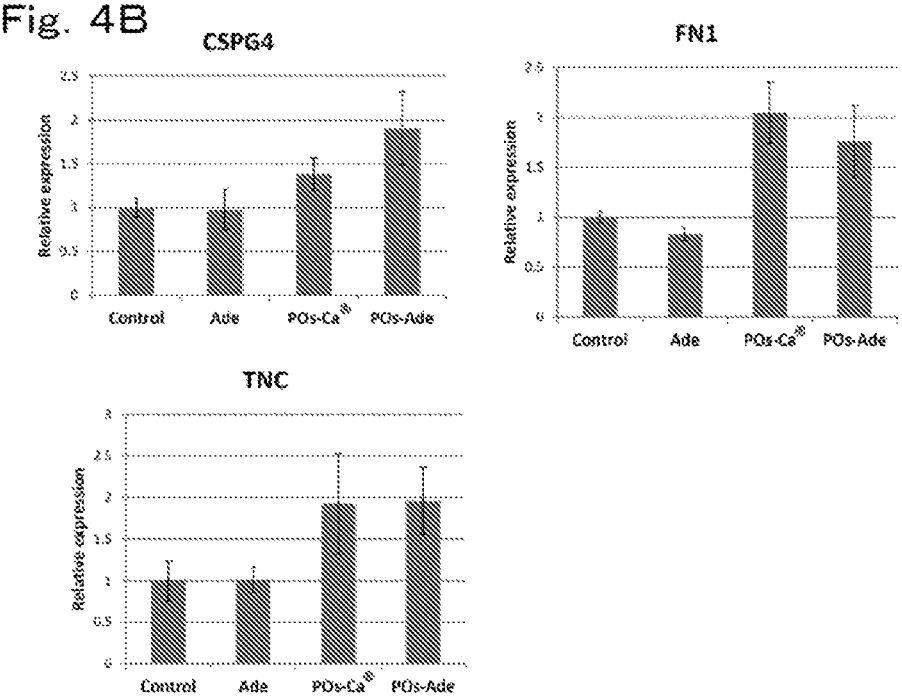

n=4, Dunnett's test, bar: $p<0.05$

Fig. 6
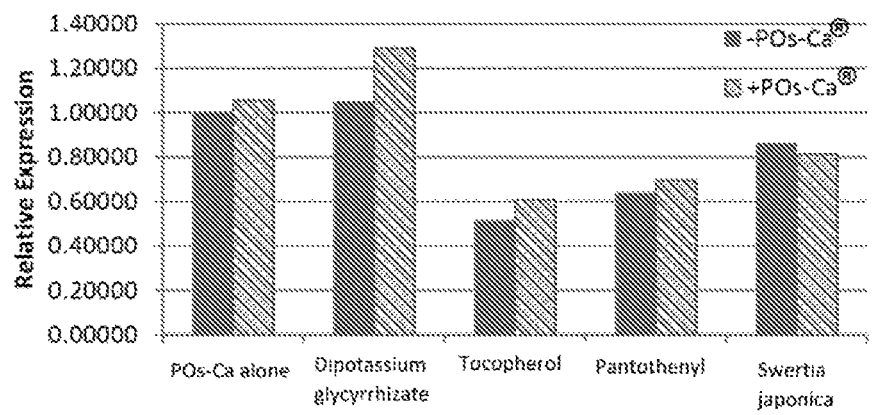
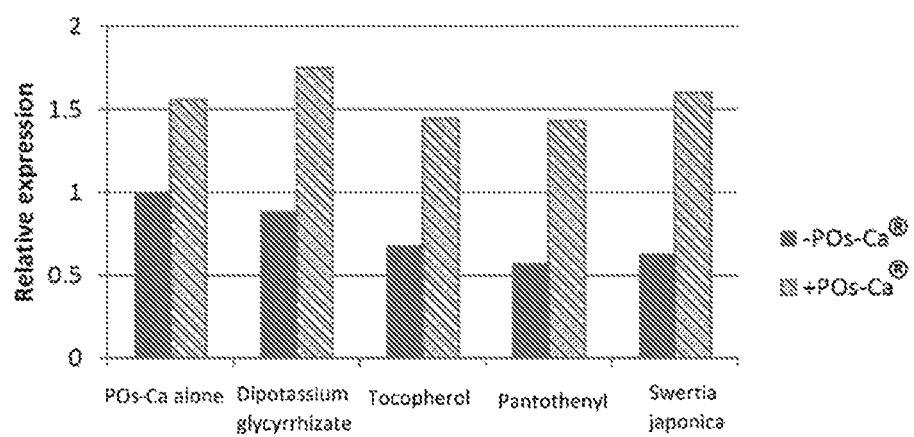

SEQUENCE LISTING

<160> NUMBER OF SEQ IDS NOS: 22

<210> SEQ ID NO 1
<211> LENGTH: 20
<212> TYPE: DNA
<213> ORGANISM: artificial sequence
<220> FEATURE:
<223> OTHER INFORMATION: FN1 primer 1

<400> SEQUENCE: 1
cccatcagca ggaacacctt                                           20

<210> SEQ ID NO 2
<211> LENGTH: 22
<212> TYPE: DNA
<213> ORGANISM: artificial sequence
<220> FEATURE:
<223> OTHER INFORMATION: FN1 primer 2

<400> SEQUENCE: 2
ggctcactgc aaagactttg aa                                        22

<210> SEQ ID NO 3
<211> LENGTH: 20
<212> TYPE: DNA
<213> ORGANISM: artificial sequence
<220> FEATURE:
<223> OTHER INFORMATION: CSPG4 primer 1

<400> SEQUENCE: 3
agctagccag gactgatgga                                           20

<210> SEQ ID NO 4
<211> LENGTH: 20
<212> TYPE: DNA
<213> ORGANISM: artificial sequence
<220> FEATURE:
<223> OTHER INFORMATION: CSPG4 primer 2

<400> SEQUENCE: 4
cagcctaacc tgctccaaag                                           20

<210> SEQ ID NO 5
<211> LENGTH: 20
<212> TYPE: DNA
<213> ORGANISM: artificial sequence

```
<220> FEATURE:
<223> OTHER INFORMATION: TNC primer 1

<400> SEQUENCE: 5
agggaccact gggtgagaga                                            20

<210> SEQ ID NO 6
<211> LENGTH: 22
<212> TYPE: DNA
<213> ORGANISM: artificial sequence
<220> FEATURE:
<223> OTHER INFORMATION: TNC primer 2

<400> SEQUENCE: 6
gggctggttg tattgatgct tt                                         22

<210> SEQ ID NO 7
<211> LENGTH: 20
<212> TYPE: DNA
<213> ORGANISM: artificial sequence
<220> FEATURE:
<223> OTHER INFORMATION: VCAN primer 1

<400> SEQUENCE: 7
caagcatcct gtctcacgaa                                            20

<210> SEQ ID NO 8
<211> LENGTH: 20
<212> TYPE: DNA
<213> ORGANISM: artificial sequence
<220> FEATURE:
<223> OTHER INFORMATION: VCAN primer 2

<400> SEQUENCE: 8
caacggaagt catgctcaaa                                            20

<210> SEQ ID NO 9
<211> LENGTH: 19
<212> TYPE: DNA
<213> ORGANISM: artificial sequence
<220> FEATURE:
<223> OTHER INFORMATION: ALPL primer 1

<400> SEQUENCE: 9
gacccttgac ccccacaat                                             19

<210> SEQ ID NO 10
<211> LENGTH: 19
<212> TYPE: DNA
<213> ORGANISM: artificial sequence
<220> FEATURE:
<223> OTHER INFORMATION: ALPL primer 2

<400> SEQUENCE: 10
gctcgactgc atgtcccct                                             19

<210> SEQ ID NO 11
<211> LENGTH: 20
<212> TYPE: DNA
<213> ORGANISM: artificial sequence
<220> FEATURE:
<223> OTHER INFORMATION: WNT5A primer 1

<400> SEQUENCE: 11
agggctccta cgagagtgct                                            20
```

```
<210> SEQ ID NO 12
<211> LENGTH: 18
<212> TYPE: DNA
<213> ORGANISM: artificial sequence
<220> FEATURE:
<223> OTHER INFORMATION: WNT5A primer 2

<400> SEQUENCE: 12
gacaccccat ggcacttg                                                 18

<210> SEQ ID NO 13
<211> LENGTH: 20
<212> TYPE: DNA
<213> ORGANISM: artificial sequence
<220> FEATURE:
<223> OTHER INFORMATION: VEGFA primer 1

<400> SEQUENCE: 13
ctacctccac catgccaagt                                               20

<210> SEQ ID NO 14
<211> LENGTH: 20
<212> TYPE: DNA
<213> ORGANISM: artificial sequence
<220> FEATURE:
<223> OTHER INFORMATION: VEGFA primer 2

<400> SEQUENCE: 14
agctgcgctg atagacatcc                                               20

<210> SEQ ID NO 15
<211> LENGTH: 20
<212> TYPE: DNA
<213> ORGANISM: artificial sequence
<220> FEATURE:
<223> OTHER INFORMATION: VEGFB primer 1

<400> SEQUENCE: 15
gcagatcctc atgatccggt                                               20

<210> SEQ ID NO 16
<211> LENGTH: 20
<212> TYPE: DNA
<213> ORGANISM: artificial sequence
<220> FEATURE:
<223> OTHER INFORMATION: VEGFB primer 2

<400> SEQUENCE: 16
ggcttcacag cactgtcctt                                               20

<210> SEQ ID NO 17
<211> LENGTH: 21
<212> TYPE: DNA
<213> ORGANISM: artificial sequence
<220> FEATURE:
<223> OTHER INFORMATION: FGF7 primer 1

<400> SEQUENCE: 17
tgtcgaacac agtggtacct g                                             21

<210> SEQ ID NO 18
<211> LENGTH: 20
<212> TYPE: DNA
<213> ORGANISM: artificial sequence
<220> FEATURE:
<223> OTHER INFORMATION: FGF7 primer 2
```

```
<400> SEQUENCE: 18
ccctttgatt gccacaattc                                                20

<210> SEQ ID NO 19
<211> LENGTH: 20
<212> TYPE: DNA
<213> ORGANISM: artificial sequence
<220> FEATURE:
<223> OTHER INFORMATION: PGK1 primer 1

<400> SEQUENCE: 19
agggaaaaga tgcttctggg                                                20

<210> SEQ ID NO 20
<211> LENGTH: 24
<212> TYPE: DNA
<213> ORGANISM: artificial sequence
<220> FEATURE:
<223> OTHER INFORMATION: PGK1 primer 2

<400> SEQUENCE: 20
aagtgaagct cggaaagctt ctat                                           24

<210> SEQ ID NO 21
<211> LENGTH: 20
<212> TYPE: DNA
<213> ORGANISM: artificial sequence
<220> FEATURE:
<223> OTHER INFORMATION: GAPDH primer 1

<400> SEQUENCE: 21
acagtcagcc gcatcttctt                                                20

<210> SEQ ID NO 22
<211> LENGTH: 20
<212> TYPE: DNA
<213> ORGANISM: artificial sequence
<220> FEATURE:
<223> OTHER INFORMATION: GAPDH primer 1

<400> SEQUENCE: 22
acgaccaaat ccgttgactc                                                20
```

HAIR PAPILLA CELL ACTIVATOR

TECHNICAL FIELD

The present invention relates to the field of hair.

BACKGROUND ART

Hair growth involves division of hair matrix cells at the hair root and formation of hair by cells thus produced. Hair grows in a cycle referred to as the hair cycle, which repeats the anagen, catagen, and telogen phases. Follicle dermal papilla cells control the hair cycle by exerting an influence upon the proliferation and differentiation of hair follicle epithelial stem cells, through the production and release of growth factors. The activation of follicle dermal papilla cells and hair matrix cells is said to contribute to the hair-growth mechanism.

At hair follicles, blood vessels are actively remodeled depending on the hair cycle, and any disturbances in angiogenesis then lead to an insufficient supply of nutrients and oxygen for hair formation. A deficiency in blood flow from the hair follicle vascular network is said to involve the pathology of male pattern baldness (AGA).

The following facts are known concerning the genes of follicle dermal papilla cells in connection with hair development and hair growth. FGF-7 and IGF-1 are among known growth factors that are secreted by follicle dermal papilla cells into hair matrix cells. These genes serve to maintain the hair follicle growth. Vascular endothelial growth factor (VEGF), which is secreted by follicle dermal papilla cells, is involved in the formation of hair follicle blood vessels, and has the effect of proliferating follicle dermal papilla cells in an autocrine manner. The expression level of VEGF, however, decreases as the hair cycle transitions from the anagen phase to the catagen phase. The expression of the VEGF gene is reduced in the hair tissue of individuals with AGA (male pattern baldness). VEGFB competitively binds to VEGFR-1, which is a receptor on which VEGF acts. While VEGFB proliferates vascular endothelial cells or has blood vessel permeability-enhancing activity, its effects upon hair follicles are uncertain.

The Wnt family is known to be involved in hair follicle development. Wnt5a of the Wnt family is expressed in follicle dermal papilla cells, as well as outer root sheath cells and inner root sheath cells, is involved in the development of hair follicles, and has the effect of preventing cell death of follicle dermal papilla cells. In follicle dermal papilla cells, the expression level of Wnt5a is known to become maximal during the anagen phase (Non Patent Literature 1: PLoS One 4, e5354 (2009); Non Patent Literature 2: Acta Histochemica 113, 608-612 (2011)).

Alkaline phosphatase (ALP, ALPL) serves as an index of the activity of follicle dermal papilla cells including hair growth-inducing ability.

Versican, which is a chondroitin sulfate proteoglycan, is known to increase in hair follicles during the anagen phase and decrease toward the telogen phase (Non Patent Literature 3: J. Dermatol. Sci. 39, 147-154 (2005)), and its expression level is correlated with hair growth-inducing activity.

Various drugs having hair-restoration effects are known. Of the drugs ranked in terms of potency on a scale of 1 to 5 in "Guidelines for the Treatment of Alopecia" by the Japanese Dermatological Association, minoxidil and finasteride (for men only) are classified into the category of "strongly recommended", while adenosine is classified into the category of "the application may be considered, but lacks sufficient evidence". The guidelines also mention carpronium chloride, t-flavanone, 6-benzylaminopurine (cytopurine), pentadecane, ketoconazole, and cepharanthine.

Minoxidil has been reported to activate the SUR (sulfonylurea receptor), and thereby suppress hair matrix cell apoptosis through mitochondrial ATP-sensitive K channel opening, and have the effect of improving the hair tissue blood flow through vascular smooth muscle ATP-sensitive K channel opening and promoting the production of cell growth factors such as VEGF from follicle dermal papilla cells.

Finasteride inhibits 5 α-reductase, which is an enzyme that converts testosterone into dihydrotestosterone, and is thus effective against AGA, which is male alopecia induced by dihydrotestosterone. Finasteride, however, is not effective against forms of alopecia other than AGA such as alopecia areata.

t-Flavanone is believed to suppress the expression of TGF-β that suppresses the proliferation of hair matrix cells, thereby promoting hair growth.

6-Benzylaminopurine suppresses the expression of the NT-4 gene involved in the apoptosis of hair matrix cells in follicle dermal papilla cells, thereby growing hair and reducing hair shedding.

Adenosine directly acts on the follicle dermal papilla, and serves to promote hair growth by increasing the amount of production of a hair growth-promoting factor, FGF-7, to prolong the anagen phase of the hair cycle, thereby growing strong thick hair instead of thin weak hair.

Additionally, the following components are disclosed as having hair-restoration effects: low-molecular-weight acidic mucopolysaccharides, i.e., hyaluronic acid, chondroitin sulfate, dermatan sulfate, and heparan sulfate, in JP H05-38726 B (Patent Literature 1); sulfated polysaccharides and/or salts thereof in JP H09-188607 A (Patent Literature 2); an alginate oligosaccharide or a salt thereof in JP H10-203930 A (Patent Literature 3); sialic acid and sialic acid derivatives in JP Patent No. 2555389 (Patent Literature 4); the sulfuric acid ester and phosphate ester of β-1,3-glucan as examples of β-1,3-glucan derivatives in JP 2004-238286 A (Patent Literature 5); fucoidan in JP Patent No. 3831252 (Patent Literature 6); and an acidic xylooligosaccharide in JP Patent No. 3719207 (Patent Literature 7). These components, however, are neither disclosed nor suggested to act on follicle dermal papilla cells. Hair-restoration effects have also been obtained with sodium salts of these components.

JP Patent No. 2583812 (Patent Literature 8) discloses that a hair-nourishment effect is enhanced by exchanging cations of at least one acidic polysaccharide selected from the group consisting of alginic acid, carrageenan, pectin, and dextran sulfate, with hydrogen ions.

JP Patent No. 3240102 (Patent Literature 9) discloses that a phosphorylated saccharide calcium salt solubilizes calcium, and thus, is used for oral compositions or fertilizer. JP 2006-249077 A (Patent Literature 10) discloses the use of a phosphorylated saccharide calcium salt for external preparations for skin, and discloses its effects of improving the supply of minerals, promotion of collagen production in the epidermis, and water-retention effect of the skin. WO 2007/040027 (Patent Literature 11) discloses that a combination of a phosphorylated saccharide calcium salt and ascorbic acid or the like markedly improves the moisturizing effect or anti-aging, the cell-activation effect, or the whitening effect of the skin. JP 2012-77044 A (Patent Literature 12) discloses that a phosphorylated saccharide calcium salt has the effect of promoting epidermal turnover, promoting keratinocyte differentiation, and promoting tight junction formation.

CITATION LIST

Patent Literature

Patent Literature 1: JP H05-38726 B
Patent Literature 2: JP H09-188607 A
Patent Literature 3: JP H10-203930 A
Patent Literature 4: JP Patent No. 2555389
Patent Literature 5: JP 2004-238286 A
Patent Literature 6: JP Patent No. 3831252
Patent Literature 7: JP Patent No. 3719207
Patent Literature 8: JP Patent No. 2583812
Patent Literature 9: JP Patent No. 3240102
Patent Literature 10: JP 2006-249077 A
Patent Literature 11: WO 2007/040027
Patent Literature 12: JP 2012-77044 A Non Patent Literature Non Patent Literature 1: PLoS One 4, e5354 (2009)
Non Patent Literature 2: Acta Histochemica 113, 608-612 (2011)
Non Patent Literature 3: J. Dermatol. Sci. 39, 147-154 (2005)

SUMMARY OF INVENTION

Solution to Problem

As a result of earnest development by the present inventors, the inventors pursued a study of an acidic saccharide alkaline earth metal salt such as phosphorylated saccharide calcium, which was known to have the effect of promoting tooth remineralization, the effect of improving the barrier function of skin, and the like, and found its effects upon hair. The present inventors made a new finding that phosphorylated oligosaccharide calcium and its analogs have the function of activating genes that play an important role in the growth of hair, for follicle dermal papilla cells that control the hair cycle and hair growth. Furthermore, the present inventors found that phosphorylated oligosaccharide calcium and its analogs also have the effect of promoting the proliferation of follicle dermal papilla cells. Thus, acidic saccharide alkaline earth metal salts including phosphorylated oligosaccharide calcium are believed to be applicable to hair-restoration purposes through the proliferation and activation of follicle dermal papilla cells. On the other hand, an acidic saccharide sodium salt has been found to lack such effects, and the use of an alkaline earth metal has been found to be advantageous. None of the documents described in the Background Art section disclose or suggest the effects of a phosphorylated saccharide calcium salt upon follicle dermal papilla cells.

Thus, the present invention provides the following aspects of invention:

(Item 1) An agent for activating proliferation of follicle dermal papilla cells comprising an acidic saccharide comprising an alkaline earth metal.

(Item 2) The agent for activating proliferation according to item 1, wherein the acidic saccharide is selected from the group consisting of a phosphorylated saccharide and lactobionic acid.

(Item 3) The agent for activating proliferation according to item 1 or 2, wherein the acidic saccharide is a phosphorylated saccharide.

(Item 4) The agent for activating proliferation according to any one of items 1 to 3, wherein the alkaline earth metal is calcium or magnesium.

(Item 5) The agent for activating proliferation according to any one of items 1 to 4, wherein the alkaline earth metal is calcium.

(Item 6) The agent for activating proliferation according to any one of items 1 to 5, wherein the acidic saccharide comprising an alkaline earth metal is lactobionic acid calcium salt, glucose-1-phosphate calcium salt (G1P-Ca), a phosphorylated oligosaccharide calcium salt (also referred to as POs-Ca (R)), or a phosphorylated oligosaccharide magnesium salt (POs-Mg).

(Item 7) The agent for activating proliferation according to any one of items 1 to 6, wherein the acidic saccharide comprising an alkaline earth metal is the phosphorylated oligosaccharide calcium salt (POs-Ca (R)).

(Item 8) The agent for activating proliferation according to any one of items 1 to 7, wherein the acidic saccharide comprising an alkaline earth metal is provided by an acidic saccharide alkaline earth metal salt, or a combination of a salt of the acidic saccharide other than an alkaline earth metal salt or the acidic saccharide, and an alkaline earth metal salt other than the acidic saccharide alkaline earth metal salt.

(Item 9) The agent for activating proliferation according to item 8, wherein the salt of the acidic saccharide other than an alkaline earth metal salt is an acidic saccharide alkali metal salt.

(Item 10) The agent for activating proliferation according to item 8 or 9, wherein the alkaline earth metal salt other than the acidic saccharide alkaline earth metal salt is a water-soluble alkaline earth metal salt.

(Item 11) The agent for activating proliferation according to any one of items 1 to 10, which is also for promoting proliferation of hair matrix cells.

(Item 12) The agent for activating proliferation according to any one of items 1 to 11, which is also for promoting proliferation of hair follicles.

(Item 13) The agent for activating proliferation according to any one of items 1 to 12, which is also for promoting proliferation of hair matrix cells and hair follicles.

(Item 14) An agent for hair restoration comprising an acidic saccharide comprising an alkaline earth metal.

(Item 15) The agent for hair restoration according to item 14, which is for at least one selected from the group consisting of treatment of hair thinning, prevention of hair loss, promotion of hair restoration, and promotion of hair growth.

(Item 15A) The agent for hair restoration according to item 14 or 15, further comprising the feature according to any one of items 2 to 14.

(Item 16) An agent for hair growth comprising an acidic saccharide comprising an alkaline earth metal.

(Item 16A) The agent for hair growth according to item 14 or 16, further comprising the feature according to any one of items 2 to 14.

(Item 17) The agent for activating proliferation of follicle dermal papilla cells according to any one of items 1 to 13, the agent for hair restoration according to item 14, 15, or 15A, or the agent for hair growth according to item 16 or 16A, which further comprises another active ingredient.

(Item 18) The agent according to item 17, wherein the active ingredient comprises minoxidil.

(Item 19) An acidic saccharide comprising an alkaline earth metal, for activating proliferation of follicle dermal papilla cells.

(Item 20) A method for activating proliferation of follicle dermal papilla cells comprising the step of administering a composition comprising an effective amount of an acidic saccharide comprising an alkaline earth metal and a pharmacologically acceptable carrier to a subject in need of the activation of proliferation.

The present invention also provides the following aspects of invention:

(A1) An agent for activating proliferation of follicle dermal papilla cells comprising a combination of an alkaline earth metal and an acidic saccharide.

(A2) The agent for activating proliferation according to item A1, wherein the acidic saccharide is selected from the group consisting of a phosphorylated saccharide and lactobionic acid.

(A3) The agent for activating proliferation according to item A1 or A2, wherein the acidic saccharide is a phosphorylated saccharide.

(A4) The agent for activating proliferation according to any one of items A1 to A3, wherein the alkaline earth metal is calcium or magnesium.

(A5) The agent for activating proliferation according to any one of items A1 to A4, wherein the alkaline earth metal is calcium.

(A6) The agent for activating proliferation according to any one of items A1 to A5, wherein the combination of an alkaline earth metal and an acidic saccharide is lactobionic acid calcium salt, glucose-1-phosphate calcium salt (G1P-Ca), a phosphorylated oligosaccharide calcium salt (POs-Ca (R)), or a phosphorylated oligosaccharide magnesium salt (POs-Mg).

(A7) The agent for activating proliferation according to any one of items A1 to A6, wherein the combination of an alkaline earth metal and an acidic saccharide is a phosphorylated oligosaccharide calcium salt (POs-Ca (R)), or a combination of components that form the phosphorylated oligosaccharide calcium salt (POs-Ca (R)) upon mixing.

(A8) The agent for activating proliferation according to any one of items A1 to A7, wherein the combination of an alkaline earth metal and an acidic saccharide is the phosphorylated oligosaccharide calcium salt (POs-Ca (R)).

(A9) The agent for activating proliferation according to any one of items A1 to A8, wherein the combination of an alkaline earth metal and an acidic saccharide is a combination of components that form the phosphorylated oligosaccharide calcium salt (POs-Ca (R)) upon mixing, and comprises calcium chloride and sodium phosphate.

(A10) The agent for activating proliferation according to any one of items A1 to A9, wherein the combination of an alkaline earth metal and an acidic saccharide is provided by an acidic saccharide alkaline earth metal salt, or a combination of a salt of the acidic saccharide other than an alkaline earth metal salt or the acidic saccharide, and an alkaline earth metal salt other than the acidic saccharide alkaline earth metal salt.

(A11) The agent for activating proliferation according to item A10, wherein the salt of the acidic saccharide other than an alkaline earth metal salt is an acidic saccharide alkali metal salt.

(A12) The agent for activating proliferation according to item A10 or 11, wherein the alkaline earth metal salt other than the acidic saccharide alkaline earth metal salt is a water-soluble alkaline earth metal salt.

(A13) The agent for activating proliferation according to any one of items A1 to A12, which is also for promoting proliferation of hair matrix cells.

(A14) The agent for activating proliferation according to any one of items A1 to A13, which is also for promoting proliferation of hair follicles.

(A15) The agent for activating proliferation according to any one of items A1 to A14, which is also for promoting proliferation of hair matrix cells and hair follicles.

(A16) An agent for hair restoration comprising a combination of an alkaline earth metal and an acidic saccharide.

(A17) The agent for hair restoration according to item A16, which is for at least one selected from the group consisting of treatment of hair thinning, prevention of hair loss, promotion of hair restoration, and promotion of hair growth.

(A18) An agent for hair growth comprising a combination of an alkaline earth metal and an acidic saccharide.

(A19) The agent for activating proliferation of follicle dermal papilla cells according to any one of items A1 to A15, the agent for hair restoration according to item A16 or A17, or the agent for hair growth according to item A18, which further comprises another active ingredient.

(A20) The agent according to item A19, wherein the active ingredient comprises minoxidil or adenosine.

(A21) The agent according to item A19, wherein the active ingredient comprises at least one selected from the group consisting of minoxidil, *Swertia japonica*, pantothenyl ethyl ether, tocopherol acetate, glycyrrhizinate dipotassium, and adenosine.

(A22) The agent according to item A19, wherein the active ingredient comprises adenosine.

(A23) An acidic saccharide comprising an alkaline earth metal, for activating proliferation of follicle dermal papilla cells.

(A24) A method for activating proliferation of follicle dermal papilla cells comprising the step of administering a composition comprising an effective amount of a combination of an alkaline earth metal and an acidic saccharide as well as a pharmacologically acceptable carrier to a subject in need of the activation of proliferation.

In the present invention, it is contemplated that further combinations of one or more of the features described above other than the disclosed combinations can be provided. Further embodiments and advantages of the present invention will be appreciated by a person skilled in the art from a reading and understanding of the following description, as required.

Advantageous Effects of Invention

The agent for activating proliferation of follicle dermal papilla cells of the present invention promotes the proliferation of follicle dermal papilla cells more than general calcium agents. The agent for activating proliferation of the present invention activates CSPG4, Wnt5a, ALPL, tenascin C, versican, fibronectin, and VEGF, which are not activated by general calcium agents. The agent for activating proliferation of the present invention also promotes the expression of FGF-7. Suppression of follicle dermal papilla cell apoptosis is demonstrated by the promotion of the expression of Wnt5a. Hair-follicle angiogenesis is demonstrated by the expression of VEGF. Promotion of hair matrix cell proliferation is demonstrated by the expression of FGF-7. Promotion of the activity of follicle dermal papilla cells is demonstrated by the promotion of the expression of ALPL and versican. Versican is an extracellular matrix specific to follicle dermal papilla cells. Promotion of anagen-phase hair follicles is demonstrated by the expression of tenascin C. Promotion of anagen-phase hair follicles is demonstrated by an increase in the expression of CSPG4. Fibronectin is an extracellular matrix that is extensively present, and is expected to promote follicle dermal papilla cells and the like. Through the upregulation of these genes, follicle dermal papilla cells demonstrate the function of hair-growth phase to promote hair growth. The agent for activating proliferation of the present invention has the effect of suppressing the expression of VEGFB, which is upregulated when general calcium agents are administered. When used in combination with minoxidil, the agent for activating proliferation of the present invention produces its effects in an additive manner (complementarily). That is, it is believed that the agent for activating proliferation of the present invention, when used in combination with minoxidil, can achieve further promotion of hair growth, through the combination of its mechanism with the other mechanism. The agent for activating proliferation of the present invention can be prepared at relatively low cost, and differs from conventional hair-restoration agents developed for pharmaceutical purposes in that the agent for activating proliferation can be used not only as a pharmaceutical product but also as a cosmetic product or a quasi drug.

Although the effects of an acidic saccharide alkaline earth metal salt such as POs-Ca (R) as external preparations for skin for the purpose of moisturizing, enhancing the barrier function, and the like have been previously revealed, its effects upon hair have been uncertain, and particularly its effects upon follicle dermal papilla cells have not even been suggested. Raw materials having hair-restoration effects that have been previously reported include minoxidil, finasteride, and carpronium chloride as main ingredients for pharmaceutical products, as well as t-flavanone, cytopurine, pentadecane, adenosine, and plant extracts such as *ginseng* extract and *Swertia japonica* extract as active ingredients for quasi drugs. Each of these raw materials, however, has a different mechanism of action, and many of them are even uncertain in terms of mechanism of action. Thus, a combination of many raw materials having different influences upon the expression of genes will be effective to activate a comprehensive group of genes important for hair restoration and hair growth. The present invention is useful in that it provides a novel raw material for hair growth.

Furthermore, although drugs registered as pharmaceutical products rather have the drawback of being limited in their use as cosmetic or food products, the acidic saccharide alkaline earth metal salt of the present invention, which is extensively used as a food or cosmetic product, and has been confirmed to be safe, is expected to have less adverse effects on patients than conventional hair-restoration agents or hair-growth agents developed as pharmaceutical products.

Thus, the agent for activating proliferation of follicle dermal papilla cells of the present invention allows an acidic saccharide calcium salt or an acidic saccharide magnesium salt that appropriately chelates with an alkaline earth metal ion such as calcium or magnesium to act on follicle dermal papilla cells, thereby providing an effect different from those of the previously reported drugs, on the expression of hair growth-related genes, and demonstrating the effect of promoting hair growth.

BRIEF DESCRIPTION OF DRAWINGS

FIG. 1D shows the results of follicle dermal papilla cell proliferation tests using POs-Ca (R) formed ultimately by mixing POs-Na and calcium chloride. The results indicated that all the concentrations tested, even less than 0.1%, of POs-Ca (R) formed ultimately by mixing POs-Na and calcium chloride, have the effect of proliferating follicle dermal papilla cells, as working concentrations. Means±standard deviations are shown, and $p<0.05$, Dunnett's test, is shown by the lines each connecting black circles.

FIG. 1E shows the results of follicle dermal papilla cell proliferation tests using each of the components shown in FIG. 1D (POs-Na and calcium chloride) alone. Means±standard deviations are shown, and there was no pair showing a significant difference as tested by Dunnett's test, $p<0.05$. The proliferation of follicle dermal papilla cells was not observed with either component, which indicated that both components were required.

FIG. 3 shows an experiment for comparison of POs-Ca (R) and minoxidil on the expression of various genes. In each graph, the bars show the control, minoxidil and POs-Ca (R) from the left. The control was taken as 1. The graphs in the upper section show FGF-7, VEGF, and Wnt5a from the left, the graphs in the middle section show ALPL, versican, and VEGFB from the left, and the graphs in the lower section show fibronectin, tenascin C, and CSPG4 from the left. Means±standard deviations are shown, and $p<0.05$, Dunnett's test, is shown by *.

FIG. 4A shows the results of observation of variations in the expression of genes induced by the combination of POs-Ca (R) and adenosine. The graph in the upper panel shows FGF7, and the graphs in the lower panel show VEGF, VCAN, and WNT5A from the left. The experiment was performed by incubating a combination of 0.25% of POs-Ca (R) and 50 μM of adenosine in DMEM (serum-free) at 37° C. for 5 hours. A significant difference was present in all of adenosine, POs-Ca (R), and POs-Ca (R)+adenosine, in Dunnett's test, $p<0.05$ (n=8). For FGF7, the combination of POs-Ca (R) and adenosine was shown to synergistically work. For VEGF, VCAN, and WNTSA, the combination of POs-Ca (R) and adenosine made an additive contribution.

FIG. 4B is a continuation of FIG. 4A, which shows the results of an experiment similarly performed on other genes (CSPG4, FN1, and TNC). The presence of a significant difference was observed with POs-Ca (R) and the combination of POs-Ca (R) and adenosine, in Dunnett's test, $p<0.05$ (n=8). POs-Ca (R) and adenosine made an additive contribution.

FIG. 6 shows the results of observation of variations in the expression of genes induced by the combinations of POs-Ca (R) and general hair-restoration components. The experiment was performed by observing the effects of the combination of 0.25% of POs-Ca (R) with glycyrrhizinate dipotassium (0.25%), tocopherol acetate (1%), pantothenyl ethyl ether (0.125%), or *Swertia japonica* (1%) as an additional component in DMEM (serum-free). The graph in the upper panel shows the effects upon FGF7, and the graph in the lower panel shows the effects upon VEGF. Each graph shows, from the left, POs-Ca (R) alone, the combination of POs-Ca (R) and glycyrrhizinate dipotassium (0.25%), the combination of POs-Ca (R) and tocopherol acetate (1%), the combination of POs-Ca (R) and pantothenyl ethyl ether (0.125%), and the combination of POs-Ca (R) and *Swertia japonica* (1%). In each pair of bars, the left bar shows the case without POs-Ca (R), and the right bar shows the case combined with POs-Ca (R).

DESCRIPTION OF EMBODIMENTS

Figure 1A:
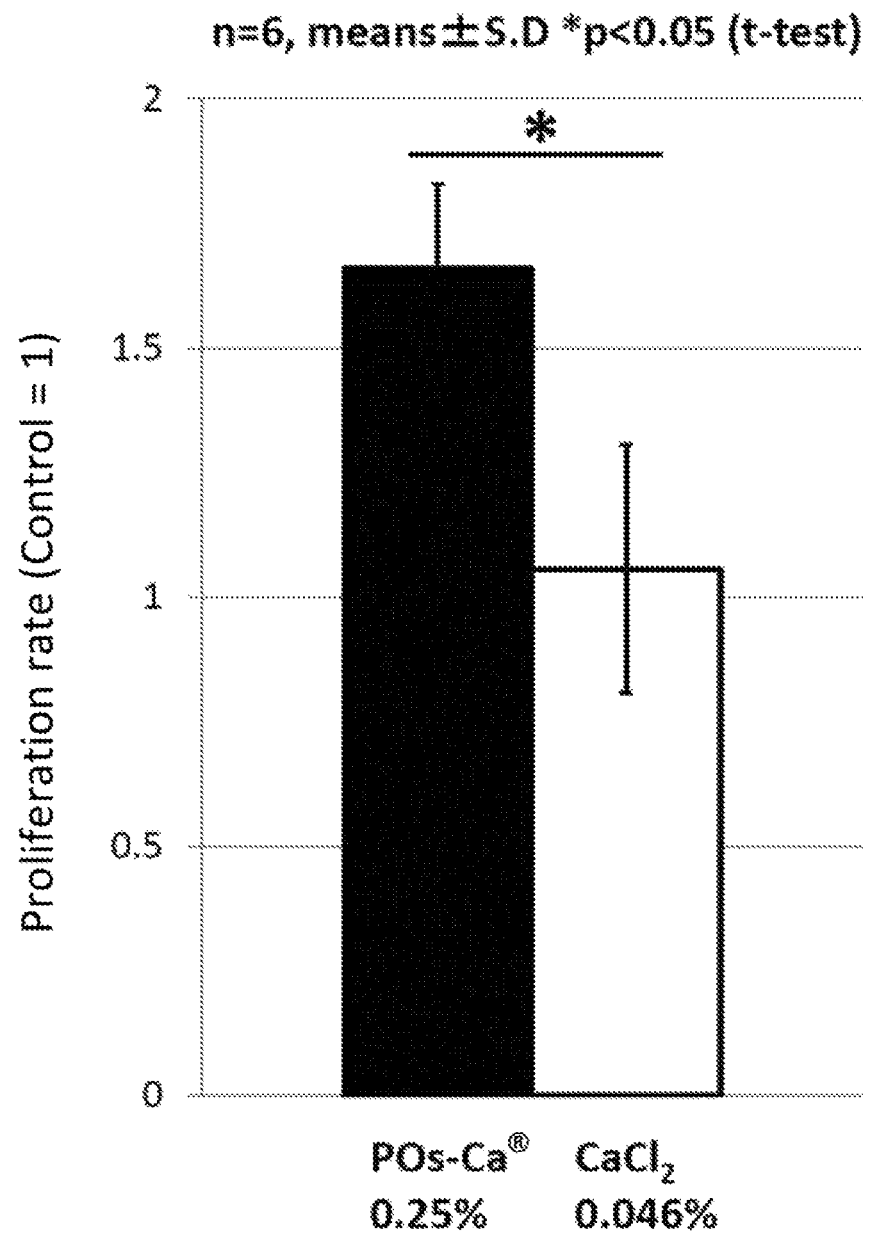
FIG. 1A shows a comparison of the cell proliferation rate between substances of different calcium species. The proliferation rate is shown relative to the control as 1. The left bar represents POs-Ca (R), and the right bar represents calcium chloride containing an equivalent amount of calcium.

The present invention will be hereinafter described. Throughout the specification, it should be understood that singular forms include the plural concept, unless otherwise mentioned. It should therefore be understood that articles for singular forms (for example, "a", "an", and "the" in English) include the plural concept, unless otherwise mentioned. It should also be understood that the terms used herein are used in the sense commonly employed in the pertinent field, unless otherwise mentioned. Thus, all scientific and technical terms used herein have the same meanings as commonly understood by a person skilled in the art to which the present invention pertains, unless otherwise defined. In the case of a contradiction, the present specification (including the definitions) takes precedence.

(Agent for Activating Proliferation of Follicle Dermal Papilla Cells, Agent for Hair Restoration and Agent for Hair Growth, Comprising Acidic Saccharide Alkaline Earth Metal Salt)

In one aspect, the present invention provides an agent for activating proliferation of follicle dermal papilla cells, an agent for hair restoration, or an agent for hair growth, comprising an acidic saccharide alkaline earth metal salt. The present invention has demonstrated that the use of an acidic saccharide alkaline earth metal salt leads to a hitherto-unexpected effect of activating the proliferation of follicle dermal papilla cells. The present invention has also been shown to achieve positive effects on various hair-related genes. For example, suppression of follicle dermal papilla cell apoptosis is demonstrated by the promotion of the expression of Wnt5a. Hair-follicle angiogenesis is demonstrated by enhanced expression of VEGF. Promotion of hair matrix cell proliferation is demonstrated by enhanced expression of FGF-7. Promotion of the activity of follicle dermal papilla cells is demonstrated by promotion of the expression of ALPL and versican. Versican is an extracellular matrix specific to follicle dermal papilla cells, and the activation of follicle dermal papilla cells is demonstrated by the upregulation of versican. Promotion of anagen-phase hair follicles is demonstrated by promotion of the expression of tenascin C. Promotion of anagen-phase hair follicles is demonstrated by promotion of the expression of CSPG4. Fibronectin is an extracellular matrix that is extensively present, and promotion of follicle dermal papilla cells or the like is demonstrated by promotion of the expression of this extracellular matrix. Through the upregulation of these genes, follicle dermal papilla cells demonstrate the function of hair-growth phase to promote hair growth. The agent for activating proliferation of follicle dermal papilla cells, the agent for hair restoration, or the agent for hair growth of the present invention has the effect of suppressing the expression of VEGFB, which is upregulated when general calcium agents are administered. The present invention has shown that hair-restoration and hair-growth effects such as treatment of hair thinning, prevention of hair loss, promotion of hair restoration, and promotion of hair growth can be achieved by demonstrating these effects. The agent for activating proliferation of follicle dermal papilla cells, the agent for hair restoration, or the agent for hair growth of the present invention further comprises another active ingredient, and examples of such active ingredients include, but are not limited to, minoxidil.

The term "acidic saccharide alkaline earth metal salt" as used herein is used in the same sense as commonly employed in the pertinent field, and refers to a salt of an acidic saccharide and an alkaline earth metal. When the salt exists as an aqueous solution, it is understood that its ionic form and the like are also included.

The term "acidic saccharide" as used herein refers to any saccharide containing an acidic group. Examples of acidic groups that can be used include, but are not limited to, inorganic acid groups such as a phosphate group and a sulfate group, and organic acid groups such as a carboxy group.

The term "alkaline earth metal" as used herein refers to any metal belonging to the group IIa of the periodic table, and examples of such metals in the present invention generally include calcium, strontium, magnesium, and barium. Calcium or magnesium is preferred as the alkaline earth metal used herein, although not limited thereto. When the alkaline earth metal is provided as a combination of an alkaline earth metal and an acidic saccharide (acidic saccharide comprising an alkaline earth metal) in the present invention, it may be provided as an acidic saccharide alkaline earth metal salt, or a combination of a salt of the acidic saccharide other than an alkaline earth metal salt or the acidic saccharide, and a water-soluble alkaline earth metal salt. In one preferred embodiment, the acidic saccharide alkaline earth metal salt may be a phosphorylated oligosaccharide calcium salt (POs-Ca (R)).

In one embodiment of the present invention, the term "salt" includes, for example, an anionic salt formed by any acidic group (for example, a phosphate group), and a cationic salt formed by any basic group or basic substance (for example, an alkaline earth metal). The "salt" can be provided in the present invention by providing an acidic saccharide having an intended acidic group and a salt having an intended basic group or basic substance (alkaline earth metal), and combining them at an appropriate time.

The term "follicle dermal papilla cells" as used herein refers to cells constituting the follicle dermal papilla at the tip of the hair bulb. The part of the hair above the epidermis is referred to as the "hair shaft", the part of the hair below the epidermis is referred to as the "hair root", and the bulge at the bottom of the hair-root part constitutes the "hair bulb". The follicle dermal papilla is said to absorb nutrients from blood capillaries to allow hair growth.

The term "hair follicle" as used herein may also be referred to as folliculus pili, and refers to the tissue covering the hair root. The hair follicle protects the hair root, and constitutes a passage through which the hair elongates.

The term "activating proliferation" as used herein in connection with follicle dermal papilla cells means that the proliferation rate is increased compared to that without any treatment. When the proliferation of follicle dermal papilla cells is activated, the cycle of hair regeneration is promoted, leading to the effect of increasing the hair that is already present, meaning that the hair-restoration effect is demonstrated. Concerning the relationship between follicle dermal papilla cells and the hair-restoration effect, for example, the Journal of Pharmacological Sciences 133, 73-77 (2009) describes, on page 75, an evaluation system for a follicle dermal papilla cell proliferation test as an evaluation system aimed at creating an anti-male pattern baldness (AGA) drug, and describes that promoting the proliferation of follicle dermal papilla cells is important for the formation of hair that is thick and strong. The Journal of Pharmacological Sciences 119, 167-174 (2002) also discloses, in "6. Hair-Growth Mechanism of Minoxidil" on page 170, the action of proliferating follicle dermal papilla cells as specific action, in the discussion of the hair-growth effect of minoxidil. Furthermore, "Functional Cosmetology Substantiation of Cosmetics Efficacy: Recent Progress and Future Promise" (supervised by the Society of Cosmetic Chemists of Japan) introduces, as an in vitro evaluation system for hair-restoration agents, follicle dermal papilla cell culture and the quantification of proliferation rate or growth factors as primary screening. It is thus recognized in the pertinent field that the hair-restoration effect can be said to be demonstrated to a certain degree by means of follicle dermal papilla cell culture and the quantification of proliferation rate or growth factors.

The term "hair growth" as used herein refers to growing new hair, and includes the effect of growing hair from a pore from which the hair has been lost.

The term "hair restoration" as used herein refers to the concept encompassing preventing the shedding of, and promoting the growth of, the hair that is already present, and also includes the effect of growing hair that is now growing, including downy hair, to be thick and strong.

In one embodiment, the hair-restoration effect can be evaluated using the rate of hair elongation as an index. The hair-restoration effect refers to promoting the elongation of hair, increasing the thickness of hair, promoting the transition of the hair cycle from the telogen phase to anagen phase, and/or inhibiting the transition of the hair cycle from the anagen phase to the catagen phase, which results in an increase in the amount of hair. Thus, the "hair restoration" encompasses the concept of growing hair, nourishing hair, and preventing hair loss. The hair-restoration effect may be measured, for example, using a method that involves organ-culturing isolated hair follicles, and measuring the amount of elongation of hair during the culture period, although the method is not particularly limited thereto.

The term "agent for promoting proliferation of follicle dermal papilla cells" as used herein refers to an agent for promoting the proliferation of follicle dermal papilla cells, and means that the addition of the agent for promoting proliferation of follicle dermal papilla cells augments, preferably statistically significantly, the proliferation of follicle dermal papilla cells, compared to that without the addition of the same.

The term "agent for hair growth" as used herein refers to any agent having the hair-growth effect.

The term "agent for hair restoration" as used herein refers to any agent having the hair-restoration effect.

The term "pharmaceutical product" as used herein refers to products intended to be used for diagnosing, treating, or preventing diseases in humans or animals, which are not mechanical instruments, dental materials, medical articles, and sanitary articles; or products intended to exert an influence upon the structure or function of the body of a human or an animal, which are not mechanical instruments, dental materials, medical articles, and sanitary articles. The definition of pharmaceutical products does not include quasi drugs and cosmetic products.

An exemplary range of efficacy of a pharmaceutical product related to hair includes items concerning the improvement of hair thinning such as alopecia areata, seborrheic alopecia, diffuse alopecia, senile alopecia, and AGA, or the promotion of hair growth, for example, which are recognized by the Ministry of Health, Labor and Welfare.

The term "quasi drug" as used herein refers to (1) products intended to prevent nausea or other unpleasantness, or foul breath or body odor; prevent miliaria, fester, and the like; prevent hair loss, grow hair, or remove hair; or eliminate or prevent rodents, flies, mosquitoes, fleas, and the like for the health of humans or animals, which products have mild action on human bodies, and which are not mechanical instruments, dental materials, medical articles, and sanitary articles, or (2) products intended to be used for diagnosing, treating, or preventing diseases in humans or animals, or products intended to exert an influence upon the structure or function of the body of a human or an animal, which are designated by the Minister of Health, Labor and Welfare. In a country outside Japan, the law of that country takes precedence over the definitions of the "pharmaceutical product" and "quasi drug" given herein.

An exemplary range of efficacy of a quasi drug related to hair includes hair growth, prevention of hair thinning, itchiness, and hair loss, promotion of hair restoration, promotion of hair growth, hair loss after disease or delivery, and hair nourishment.

The phrase "pharmacologically acceptable" as used herein means being approved by the governmental supervisory authority, or being listed in the Pharmacopoeia or other commonly accepted pharmacopoeia, for use in animals, more specifically humans.

The term "subject" as used herein refers to a subject, preferably a human, to be prevented or treated, for example, using the agent of the present invention.

The term "carrier" as used herein refers to a diluent, an adjuvant, an excipient, or a vehicle for administering the therapeutic agent in conjunction. Such carriers can be sterile liquids such as water and oil, and include those of petroleum, animal, plant, or synthetic origin, including, but are not limited thereto, peanut oil, soybean oil, mineral oil, and sesame oil.

(Materials Used in the Present Invention)

A combination of any acidic saccharide and any alkaline earth metal is used as the acidic saccharide comprising an alkaline earth metal used in the present invention. The acidic saccharide comprising an alkaline earth metal can be provided in the form of an acidic saccharide alkaline earth metal salt, or by a combination of a salt of the acidic saccharide other than an alkaline earth metal salt or the acidic saccharide, and a water-soluble alkaline earth metal salt.

Any acidic saccharide can be used as the acidic saccharide used in the present invention, and examples thereof include, but are not limited to, acidic polysaccharides including phosphorylated saccharides, sulfated saccharides, uronic acid, lactobionic acid, maltobionic acid, alginic acid, and fucoidan, or reducing sugars thereof, or aldaric acids or aldonic acids thereof. A preferred example is a phosphorylated saccharide or lactobionic acid, and a more preferred example is a phosphorylated saccharide.

In one preferred embodiment, the acidic saccharide used in the present invention includes a phosphorylated oligosaccharide or its sugar alcohol. The phosphorylated oligosaccharide can be prepared from potato starch. Generally, the phosphorylated oligosaccharide is a glucan composed of 3 to 5 glucose units bound by α-1,4 linkages, and to which one phosphate group is bound, and/or a glucan composed of 2 to 8 glucose units bound by α-1,4 linkages, and to which two phosphate groups are bound.

In one embodiment, examples of alkaline earth metals used in the present invention include calcium, strontium, magnesium, and barium, with calcium or magnesium being preferred, and calcium being more preferred.

In a more preferred embodiment, a phosphorylated oligosaccharide calcium salt (POs-Ca (R)) can be used in the present invention.

(Phosphorylated Oligosaccharide)

The above-described phosphorylated oligosaccharide can be prepared from a starch in which many phosphate groups are bound, such as crude potato starch. In potato starch, a relatively large number of phosphate groups are bound by ester linkages to the 3- and 6-positions of the glucose units constituting the potato starch. The phosphate groups are mainly present in amylopectin.

For enzymatic degradation of a starch or the like, one or more of α-amylase (EC 3.2.1.1), β-amylase (EC 3.2.1.2), glucoamylase (EC 3.2.1.3), isoamylase (EC 3.2.1.68), pullulanase (EC 3.2.1.41), and neopullulanase (Kuriki et al., Journal of Bacteriology, vol. 170, pp. 1554-1559, 1988) as amylolytic enzymes, and cyclodextrin glucanotransferase (EC 2.4.1.19; hereinafter abbreviated as CGTase) as a glycosyltransferase, are acted, or one or more of these enzymes are used in combination with α-glucosidase (EC 3.2.1.20).

When the starch is degraded by isoamylase or pullulanase, a phosphorylated saccharide without branches can be obtained by cleaving α-1,6 branches in the starch. Alternatively, when these enzymes are not used, a phosphorylated saccharide with α-1,6 branches can be obtained. Furthermore, when the starch is degraded by glucoamylase, unphosphorylated glucose units bound to the non-reducing end can be sequentially released. By means of such an enzymatic treatment, the number of phosphate groups per molecular weight of the phosphorylated saccharide after purification can be increased or decreased.

By reacting a plurality of enzymes simultaneously, the enzymatic degradation reactions are allowed to proceed simultaneously. In brief, the starch used as the raw material is dissolved in water or a buffer adjusted to a pH at which the enzymes can act. To this reaction solution, liquefying α-amylase, pullulanase, glucoamylase, and the like are added simultaneously, and reacted by heating. Using this method, while the starch is being gelatinized, neutral sugars can be released, unphosphorylated glucose units bound to the non-reducing end of the phosphorylated saccharide can be released, or α-1,6 branches derived from the raw material in the phosphorylated saccharide structure can be cleaved. With this method, a phosphorylated saccharide having an increased phosphate content can be obtained by a one-step reaction, rather than a two-step reaction.

When enzymatic reactions are performed in two or more steps by allowing a plurality of enzymes to act in individual steps, the order of the enzymes to be acted is not specified. If the starch concentration is high, however, it is preferred that an enzyme incorporating liquefying α-amylase is initially acted. If isoamylase or pullulanase is initially acted, the amylose content will increase. Because amylose is more readily retrograded and precipitated than amylopectin, the raw material will be retrograded and precipitated. The raw material then will not be acted upon by other enzymes.

The amylolytic enzyme, glycosyltransferase, and α-glucosidase used may be of any origin. For example, as the origin of α-amylase, an amylolytic enzyme preparation from *Bacillus* bacteria or *Aspergillus* bacteria can be suitably used. The enzymatic reactions may be performed at a temperature and a pH at which the enzymes can act. For example, a temperature of 25 to 70° C. and a pH of 4 to 8 are suitably used.

Initially, the starch used as the raw material is dissolved in water or a buffer adjusted to a pH at which the enzymes can act. To this solution, liquefying α-amylase is added, and reacted by heating, thereby liquefying and gelatinizing the starch. The liquefying α-amylase is subsequently maintained at a temperature of 20 to 80° C. for an appropriate duration. The liquefying α-amylase to be acted may be used in a small or excess amount, as long as it can liquefy the starch. A suitable amount of the liquefying α-amylase to be acted is 20 to 50,000 U. In this case, the duration of maintaining the liquefying α-amylase is not limited as long as the starch is liquefied to such an extent that it does not undergo retrograding in subsequent steps. The liquefying α-amylase is preferably maintained at 20 to 80° C. for 30 minutes.

After the completion of the liquefaction, the enzymes do not particularly need to be inactivated; however, the enzymes may be inactivated using a conventional method, for example, by maintaining them at 100° C. for 10 minutes. Furthermore, insoluble matter may be removed by separation, using a conventional method such as centrifugation or membrane filtration. Although the phosphorylated saccharide may be subsequently fractionated, the following operation is additionally performed to obtain a phosphorylated saccharide having an increased phosphate content.

In brief, after the raw material is liquefied, it is saccharified by adding glucoamylase, isoamylase, pullulanase, and α-glucosidase thereto simultaneously or in an appropriate order, and then reacted at a temperature of 40 to 60° C. for 30 minutes to 40 hours, for example. As a result, neutral sugars and unphosphorylated glucose units bound to the non-reducing end of the phosphorylated saccharide can be released, and α-1,6 branches derived from the raw material in the phosphorylated saccharide structure can be cleaved. When glucoamylase, isoamylase, and pullulanase are used in combination, they may be combined in any manner, and may be added in any order. The amounts of the enzymes to be added and the duration of maintaining the enzymes may be determined depending on the phosphate content or the like required in the phosphorylated oligosaccharide. Preferably, 50 to 700 U of glucoamylase, 2 to 100 U of each of isoamylase and pullulanase, and 50 to 700 U of α-glucosidase may be added. The enzymes can also be suitably used in an immobilized form.

After the completion of the reaction of each of the enzymes, the enzymes do not particularly need to be inactivated; however, the enzymes may be inactivated using a conventional method, for example, by maintaining them at 100° C. for 10 minutes. Furthermore, insoluble matter may be removed by separation, using a conventional method such as centrifugation or membrane filtration.

To purify the phosphorylated oligosaccharide from the saccharide mixture containing the phosphorylated oligosaccharide, an anion-exchange resin can be used because the phosphorylated oligosaccharide is an ionic substance unlike neutral sugars. While the resin is not particularly limited in type, those that can be suitably used include Chito Pearl BCW 2500 type (Fujibo), Amberlite IRA type (Organo), DEAE-Cellulose (Whatman), DEAE-Sephadex, QAE-Sephadex (Pharmacia), and QAE-Cellulose (Bio-Rad). The resin is equilibrated with a buffer adjusted to an appropriate pH. For example, about 10 to 50 mM acetate buffer (pH 4 to 5) can be suitably used. The equilibrated resin is packed into a column, and the saccharide mixture containing the phosphorylated oligosaccharide is charged. After the neutral sugars are washed away, the adsorbed phosphorylated oligosaccharide is eluted with an alkaline solution or a salt solution.

When the phosphorylated oligosaccharide is eluted by increasing the ionic strength of the eluate, the salt to be used is not particularly limited in type. For example, a salt such as sodium chloride, ammonium bicarbonate, potassium chloride, sodium sulfate, or ammonium sulfate can be suitably used.

When the phosphorylated oligosaccharide is eluted by changing the pH of the eluate to be alkaline, the alkali reagent to be used is not particularly limited in type. For example, ammonia, sodium carbonate, or sodium hydroxide can be used. Under strongly alkaline conditions, however, phosphate groups are eliminated from the saccharide, or the reducing end of the saccharide is oxidized. Thus, the phosphorylated oligosaccharide is preferably eluted at a pH in the range from weakly acidic to weakly alkaline, and is more preferably eluted at a pH from 3 to 8.

In this case, if the phosphorylated oligosaccharide is eluted by gradually increasing the salt concentration or the pH of the eluate, or increasing the salt concentration or the pH in a stepwise manner, components of the phosphorylated oligosaccharide can be fractionated in accordance with the number of phosphate groups bound per molecule of the phosphorylated saccharide.

To purify the phosphorylated oligosaccharide from the saccharide mixture containing the phosphorylated oligosaccharide, activated carbon can also be used instead of the anion-exchange resin. While the activated carbon to be used is not particularly limited in type, granular activated carbon that can be packed into a column is preferably used. Activated carbon is adjusted using a buffer, an acid, an alkali, a salt solution, and distilled water, so as to provide conditions to yield an ability to adsorb neutral sugars except for glucose. For example, conditions obtained by loading a column with degassed activated carbon having a uniform particle size, and washing the column with distilled water can be suitably used. By passing the sample through the column, and causing neutral sugars to be adsorbed, the phosphorylated oligosaccharide can be obtained in a flow-through fraction.

Alternatively, to purify the phosphorylated oligosaccharide from the saccharide mixture containing the phosphorylated oligosaccharide, a method may be used that involves adding an alcohol with 1 to 3 carbon atoms to precipitate the phosphorylated oligosaccharide. In brief, the phosphorylated oligosaccharide only is obtained as a precipitate by adding such an alcohol to the sample solution. When the saccharide concentration is 10% or more, the alcohol is preferably added in an amount at least 3 times by volume ratio the amount of the sample solution.

In the presence of an alkaline earth metal salt, preferably a calcium salt, in addition to the alcohol, the phosphorylated oligosaccharide more readily forms a phosphorylated oligosaccharide alkaline earth metal salt, and forms a precipitate. In the presence of an alkaline earth metal salt, therefore, compared to the case where it is precipitated with only an alcohol as previously mentioned, the phosphorylated oligosaccharide can be easily collected with only a small amount of alcohol, and the component of the present invention can be directly produced. Preferably, the purification is performed under alkaline conditions. While the alkaline earth metal salt to be used is not particularly limited in type, calcium chloride or magnesium chloride, for example, which has good solubility, can be suitably used. The precipitate formed by the addition of an alcohol is extracted using a method that is commonly employed, such as decantation, filtration, centrifugation, or the like.

A phosphorylated oligosaccharide alkaline earth metal salt may be produced by adding an alkaline earth metal salt, and removing the alkaline earth metal salt from a fraction containing the phosphorylated oligosaccharide alkaline earth metal salt separated as a precipitate, or may be directly used as a component of the present invention. The removal of the metal (desalting) can be performed using a routine method. Desalting can be easily performed using a tabletop desalting apparatus, Micro Acilyzer G3 (Asahi Kasei Corporation), for example.

This alkaline earth metal salt can be produced by collecting the above-described alcohol precipitate, as the precipitate of a phosphorylated oligosaccharide alkaline earth metal salt, which is a compound of the phosphorylated oligosaccharide and the alkaline earth metal salt. If required, an operation may be repeated that involves re-dissolving the collected precipitate in water or an appropriate solution, and adding the alcohol again. This operation can remove impurities such as neutral sugars and excess salt. An ultrafiltration membrane can also be used for the removal of impurities such as salt.

(Providing the Acidic Saccharide Alkaline Earth Metal Salt)

In one embodiment, for the purpose of providing an acidic saccharide component containing an alkaline earth metal (for example, calcium) in the present invention, the following component is used: (i) an acidic saccharide alkaline earth metal salt such as an acidic saccharide calcium salt; or (ii) a combination of a salt of an acidic saccharide (for example, an acidic saccharide alkali metal salt) other than the acidic saccharide alkaline earth metal salt (for example, an acidic saccharide calcium salt) or the acidic saccharide, and an alkaline earth metal salt (for example, a calcium salt) other than the acidic saccharide alkaline earth metal salt (for example, an acidic saccharide calcium salt); or (iii) a mixture of (i) and (ii) above. If required, other materials (for example, other agents for hair restoration, other agents for hair growth, nutritional components, and cooling agents) can be additionally used. Preferably, the alkaline earth metal salt other than the acidic saccharide alkaline earth metal salt used in (ii) is a water-soluble alkaline earth metal salt. The salt of the acidic saccharide (for example, an acidic saccharide alkali metal salt) other than the acidic saccharide alkaline earth metal salt (for example, an acidic saccharide calcium salt) or the acidic saccharide, and the salt (for example, an alkali metal salt) other than the acidic saccharide alkaline earth metal salt (for example, an acidic saccharide calcium salt), recited in (ii), can form the acidic saccharide alkaline earth metal salt (for example, an acidic saccharide calcium salt) in an aqueous solution, and can work similarly to the acidic saccharide alkaline earth metal salt (for example, an acidic saccharide calcium salt). Thus, the effect of the acidic saccharide alkaline earth metal salt (for example, an acidic saccharide calcium salt) referred to herein is believed to be similarly obtained with the combination recited in (ii). As the alkali metal for the acidic saccharide alkali metal salt that can be used in the present invention, lithium, sodium, potassium, rubidium, cesium, or francium can be used, and potassium or sodium is preferably used.

In one particular embodiment, for the purpose of providing a phosphorylated saccharide component containing calcium in the present invention, the following component is used: (i) a phosphorylated saccharide calcium salt; or (ii) a combination of a salt of a phosphorylated saccharide other than the phosphorylated saccharide calcium salt or the phosphorylated saccharide, and a calcium salt other than the phosphorylated saccharide calcium salt; or (iii) a mixture of (i) and (ii) above. If required, other materials (for example, other agents for hair restoration and agents for hair growth) can be additionally used. The salt of the phosphorylated saccharide other than the phosphorylated saccharide calcium salt or the phosphorylated saccharide, and the calcium salt other than the phosphorylated saccharide calcium salt, recited in (ii), can form the phosphorylated saccharide calcium salt in an aqueous solution, and can work similarly to the phosphorylated saccharide calcium salt. Thus, the effect of the phosphorylated saccharide calcium salt referred to herein is believed to be similarly obtained with the combination recited in (ii).

The phosphorylated saccharide used in the present invention is composed of a saccharide portion and phosphate group(s). As used herein, the term "phosphorylated saccharide" refers to a saccharide having at least one phosphate group within the molecule. As used herein, the term "salt of a phosphorylated saccharide" refers to a salt of a phosphorylated saccharide. As used herein, the term "phosphorylated saccharide inorganic salt" refers to an inorganic salt of a phosphorylated saccharide. As used herein, the term "calcium salt of a phosphorylated saccharide" refers to a calcium salt of a phosphorylated saccharide.

While the number of acidic groups (phosphate groups in the case of phosphorylation, for example) in the acidic saccharide such as a phosphorylated saccharide is preferably 10 or less, and more preferably 5 or less, per molecule of the acidic saccharide such as a phosphorylated saccharide, although not particularly limited thereto. More preferably, the number of acidic groups (for example, phosphate groups) in the acidic saccharide such as a phosphorylated saccharide is 1, 2, or 3, and particularly preferably 1 or 2, per molecule of the acidic saccharide such as a phosphorylated saccharide.

The degree of polymerization of the saccharide portion in the acidic saccharide such as a phosphorylated saccharide is preferably 2 or more, and more preferably 3 or more. The degree of polymerization of the saccharide in the phosphorylated saccharide is preferably about 100 or less, more preferably about 90 or less, more preferably about 80 or less, more preferably about 70 or less, more preferably about 60 or less, more preferably about 50 or less, more preferably about 40 or less, more preferably about 30 or less, more preferably about 20 or less, more preferably about 10 or less, more preferably about 9 or less, more preferably about 8 or less, still more preferably about 7 or less, even more preferably about 6 or less, and particularly preferably about 5 or less. When the degree of polymerization of the saccharide portion in the acidic saccharide such as a phosphorylated saccharide is 10 or less, the acidic saccharide is also referred to herein as an acidic oligosaccharide (a phosphorylated oligosaccharide in the case of a phosphorylated saccharide). The term "degree of polymerization" as used herein refers to the number of structural units, i.e., the number of monosaccharide residues. For example, the degree of polymerization of a saccharide composed of 3 glucose units is 3. The degree of polymerization also sometimes refers to an average number of structural units in the polymer molecule.

The molecular weight of the acidic saccharide such as a phosphorylated saccharide is preferably about 400 or more, more preferably about 500 or more, still more preferably about 600 or more, and particularly preferably about 700 or more. The molecular weight of a phosphorylated saccharide is preferably about 1,000,000 or less, more preferably about 100,000 or less, and still more preferably about 10,000 or less, for example, about 9000 or less, about 8000 or less, about 7000 or less, about 6000 or less, about 5000 or less, about 4000 or less, or about 3000 or less, particularly preferably 2000 or less, and 1000 or less in one embodiment.

The acidic saccharide such as a phosphorylated saccharide is in the form of an acid (specifically, in the case of a phosphorylated saccharide, hydrogen is bound to a phosphate group). In the present invention, the acidic saccharide such as a phosphorylated saccharide may be used in an ionized form (specifically, in the case of a phosphorylated saccharide, the hydrogen of the phosphate group is dissociated to form a phosphate ion), or used in the form of a salt (specifically, in the case of a phosphorylated saccharide, a phosphate ion and a base cation form a bond). In a particular embodiment, preferably, an inorganic salt of the acidic saccharide such as a phosphorylated saccharide is used. The inorganic salt of the acidic saccharide such as a phosphorylated saccharide is an alkaline earth metal salt, preferably a calcium salt or a magnesium salt. The phosphorylated saccharide in the form of a calcium salt is also referred to as phosphorylated saccharide calcium. The phosphorylated saccharide in the form of a magnesium salt is also referred to as phosphorylated saccharide magnesium. This also applies to other inorganic salts. Preferably, the phosphorylated saccharide and salts thereof used in the present invention are those disclosed in JP H08-104696 A.

The saccharide portion of the acidic saccharide such as a phosphorylated saccharide can be any saccharide residue. The saccharide portion is preferably a residue of a saccharide selected from the group consisting of a glucan, a reduced glucan, mannan, dextran, agar, cyclodextrin, fucoidan, gellan gum, locust bean gum, guar gum, tamarind gum, and xanthan gum. A glucan residue or a reduced glucan residue is preferred. The term "reduced glucan" as used herein refers to a glucan in which aldehyde at the reducing end has been reduced to an alcohol. A reduced glucan is obtained by, for example, reducing aldehyde to an alcohol by hydrogenating a glucan.

The degree of polymerization in the glucan residue or reduced glucan residue, i.e., the number of glucose residues, is preferably 2 or more, and more preferably 3 or more. The number of glucose residues is preferably about 100 or less, more preferably about 90 or less, more preferably about 80 or less, more preferably about 70 or less, more preferably about 60 or less, more preferably about 50 or less, more preferably about 40 or less, more preferably about 30 or less, more preferably about 20 or less, more preferably about 10 or less, more preferably about 9 or less, more preferably about 8 or less, still more preferably about 7 or less, even more preferably about 6 or less, and particularly preferably about 5 or less.

The number of calcium ions in acidic saccharide calcium (for example, phosphorylated saccharide calcium) is not particularly limited, and calcium ions may be bound to all of, or only some of, the acidic groups (for example, phosphate groups) present in the acidic saccharide (for example, a phosphorylated saccharide). Only one, or two, or three or more calcium ions may be bound per molecule of the phosphorylated saccharide. The number of calcium ions bound per molecule of the phosphorylated saccharide is preferably about 20 or less, more preferably about 10 or less, and still more preferably about 5 or less.

Although phosphorylated saccharide calcium is known to have the effect of tooth remineralization, the effect of promoting calcium absorption, and the effect of improving the quality of taste, its effects upon hair have been unknown.

In a preferred embodiment, a phosphorylated saccharide or an inorganic salt thereof is used wherein the saccharide portion is a glucan residue or a reduced glucan residue, and wherein at least one phosphate group is bound to the glucan residue or reduced glucan residue. In another preferred embodiment, an acidic saccharide inorganic salt (for example, a phosphorylated saccharide inorganic salt) is used wherein the saccharide portion is a glucan residue or a reduced glucan residue, and wherein one or two acidic groups such as phosphate groups are bound to the glucan residue or reduced glucan residue, and an inorganic ion is bound to each of these acidic groups such as phosphate groups.

In a further preferred embodiment, phosphorylated saccharide calcium is used wherein the saccharide portion is a glucan residue or a reduced glucan residue, and wherein at least one phosphate group is bound to the glucan residue or reduced glucan residue, and calcium is bound to at least one of these phosphate groups. In still another preferred embodiment, acidic saccharide calcium (for example, phosphorylated saccharide calcium) is used wherein the saccharide portion is a glucan residue or a reduced glucan residue, and wherein one or two acidic groups such as phosphate groups are bound to the glucan residue or reduced glucan residue, and calcium is bound to each of these acidic groups such as phosphate groups.

In still another preferred embodiment, an acidic saccharide inorganic salt (for example, a phosphorylated saccharide inorganic salt) is used wherein the saccharide portion is a glucan residue or a reduced glucan residue, and wherein the glucan residue or reduced glucan residue is composed of 3 to 5 glucose residues bound by α-1,4 linkages, at least one acidic group such as a phosphate group is bound to the glucan residue or reduced glucan residue, and an inorganic ion is bound to the acidic group such as a phosphate group.

In still another preferred embodiment, acidic saccharide calcium (for example, phosphorylated saccharide calcium) is used wherein the saccharide portion is a glucan residue or a reduced glucan residue, and wherein the glucan residue or reduced glucan residue is composed of 3 to 5 glucose residues bound by α-1,4 linkages, at least one acidic group such as a phosphate group is bound to the glucan residue or reduced glucan residue, and calcium is bound to the acidic group such as a phosphate group.

In still another preferred embodiment, an inorganic salt of an acidic saccharide (for example, an inorganic salt of a phosphorylated saccharide) is used wherein the saccharide portion is a glucan residue or a reduced glucan residue, and wherein the glucan residue or reduced glucan residue is composed of 2 to 8 glucose residues bound by α-1,4 linkages, one or two acidic groups such as phosphate groups are bound to the glucan residue or reduced glucan residue, and an inorganic ion is bound to at least one of, and preferably all of, the acidic groups such as phosphate groups.

In still another preferred embodiment, acidic saccharide calcium (for example, phosphorylated saccharide calcium) is used wherein the saccharide portion is a glucan residue or a reduced glucan residue, and wherein the glucan residue or reduced glucan residue is composed of 2 to 8 glucose residues bound by α-1,4 linkages, one or two acidic groups such as phosphate groups are bound to the glucan residue or reduced glucan residue, and calcium is bound to at least one of, and preferably all of, the acidic groups such as phosphate groups.

In still another preferred embodiment, an acidic saccharide (for example, a phosphorylated saccharide) is used wherein the saccharide portion is a glucan residue or a reduced glucan residue, and wherein the glucan residue or reduced glucan residue has, as a main chain, glucose residues bound by α-1,4 linkages, and has, as a side chain, glucose residues bound by α-1,6 linkages or α-1,4 linkages.

The acidic saccharide such as a phosphorylated saccharide and a salt thereof that can be used in the present invention may each be used as a pure single compound, or used as a mixture of a plurality of compounds. The acidic saccharide such as a phosphorylated saccharide and a salt thereof used in the present invention are preferably those disclosed in JP H08-104696 A. In accordance with the method disclosed in JP H08-104696 A, mixtures of a plurality of acidic saccharides such as phosphorylated saccharides or salts thereof are obtained. Such a mixture may be used as is, or may be separated into pure compounds, and then only a single compound may be selected and used. Acidic saccharides such as phosphorylated saccharides and salts thereof, either used alone or as a mixture, demonstrate excellent performance.

The acidic saccharide such as a phosphorylated saccharide can be produced by, for example, phosphorylating a known saccharide. The acidic saccharide inorganic salt such as a phosphorylated saccharide inorganic salt can be produced by, for example, subjecting a known saccharide to a treatment for providing an acidic saccharide, such as phosphorylation, to obtain an acidic saccharide in the form of an acid, such as a phosphorylated saccharide, and subsequently converting the acidic saccharide in the form of an acid, such as a phosphorylated saccharide, into an inorganic salt. The acidic saccharide calcium salt such as phosphorylated saccharide calcium can be produced by, for example, subjecting a known saccharide to an acidifying treatment such as phosphorylation to obtain an acidic saccharide in the form of an acid, such as a phosphorylated saccharide, and subsequently converting the acidic saccharide in the form of an acid, such as a phosphorylated saccharide, into a calcium salt. As a representative example, a method for producing phosphorylated saccharides and salts thereof is disclosed in JP H08-104696 A. Phosphorylated saccharide calcium is also sold as phosphorylated oligosaccharide calcium by Ezaki Glico Co., Ltd.

Examples of saccharides as raw materials for producing the acidic saccharide such as a phosphorylated saccharide and salts thereof include a glucan, mannan, dextran, agar, cyclodextrin, fucoidan, gellan gum, locust bean gum, guar gum, tamarind gum, and xanthan gum. The following describes a case where a glucan is used. A starch in which many phosphate groups are bound, such as a general crude plant starch, preferably crude potato starch, is suitably used, although a purified product thereof may also be used. A modified starch can also be suitably used. Alternatively, various saccharides in which acidic groups such as phosphate groups are chemically bound can be used. In potato starch, a relatively large number of phosphate groups are bound by ester linkages to the 3- and 6-positions of the glucose units constituting the potato starch. Acidic groups such as phosphate groups are mainly present in amylopectin.

In a preferred embodiment, in the case where the saccharide is a glucan, it can be obtained by degrading a starch or a modified starch having an acidic group such as a phosphate group.

In a suitable embodiment, the starch or modified starch having an acidic group such as a phosphate group is acted upon by an amylolytic enzyme, a glycosyltransferase, or a combination of one or more of the above with α-glucosidase (excluding, however, the use of α-glucosidase alone).

In a preferred embodiment, the above-described amylolytic enzyme includes one or more of α-amylase, β-amylase, glucoamylase, isoamylase, pullulanase, and neopullulanase in combination. In a preferred embodiment, the above-described glycosyltransferase is cyclodextrin glucanotransferase.

In a preferred embodiment, a glycosyltransferase is acted upon a saccharide having an acidic group such as a phosphate group, in the above-described production method. The above-described glycosyltransferase is cyclodextrin glucanotransferase.

The acidic saccharide alkaline earth metal salt such as a phosphorylated saccharide alkaline earth metal salt is produced by, for example, allowing a salt of an alkaline earth metal to act on a phosphorylated saccharide in the form of an acid. Acidic saccharide calcium such as phosphorylated saccharide calcium is produced by, for example, allowing a calcium salt to act on an acidic saccharide in the form of an acid, such as a phosphorylated saccharide.

As the acidic saccharide such as a phosphorylated saccharide and a salt thereof, products with high purity or low purity may be used. For example, the acidic saccharide such as a phosphorylated saccharide and a salt thereof may each be used as a mixture with other saccharide(s). When the concentration and content of the acidic saccharide such as a phosphorylated saccharide and a salt thereof are referred to herein, the concentration and the content are calculated based on the amount of the acidic saccharide such as a phosphorylated saccharide and the salt thereof in pure form. Thus, when a mixture containing a saccharide other than the acidic saccharide such as a phosphorylated saccharide and the salt thereof is used, the above-mentioned concentration and content are calculated based on the amount of the acidic saccharide such as a phosphorylated saccharide and the salt thereof in the mixture, rather than the amount of the entire mixture.

(Alkaline Earth Metals)

The alkaline earth metal used in the present invention may be any form of an alkaline earth metal. For example, the alkaline earth metal may be provided in the form of a salt, or as a combination of a salt of the acidic saccharide other than an alkaline earth metal salt or the acidic saccharide, and a water-soluble alkaline earth metal salt. Examples of alkaline earth metals used in the alkaline earth metal salt include calcium, strontium, magnesium, and barium. Preferably, a physiologically acceptable alkaline earth metal is used. In another preferred embodiment, calcium or magnesium is used as the alkaline earth metal.

In a particular embodiment of the present invention, calcium is used as the alkaline earth metal. When used in the form of a salt, calcium may be water-soluble, water-insoluble, or poorly water-soluble. A water-soluble calcium salt is preferred. The term "water-insoluble calcium salt" as used herein refers to a calcium salt having a solubility less than 0.1 g/100 ml $H_2O$ in water at 20° C. Examples of water-insoluble calcium salts include calcium fluoride, calcium carbonate, calcium oxalate, hydroxyapatite, calcium monohydrogen phosphate, calcium oxide, calcium citrate, calcium sulfate, calcium stearate, and calcium phosphate. The term "poorly water-soluble calcium salt" as used herein refers to a calcium salt having a solubility of 1 g/100 ml $H_2O$ or more and 5 g/100 ml $H_2O$ or less in water at 20° C. Examples of poorly water-soluble calcium salts include calcium hydroxide, calcium malate, calcium gluconate, calcium dihydrogen phosphate, and calcium benzoate. The term "water-soluble calcium salt" as used herein refers to a calcium salt having a solubility higher than 5 g/100 ml $H_2O$ in water at 20° C. The solubility in water at 20° C. of the water-soluble calcium salt used in the present invention is preferably about 2 wt % or more, more preferably about 3 wt % or more, still more preferably about 4 wt % or more, and particularly preferably about 5 wt % or more. The definition of water-soluble calcium salts includes a phosphorylated saccharide calcium salt. Other examples of such water-soluble calcium salts include calcium chloride, water-soluble calcium salts of organic acids (such as calcium lactate, calcium acetate, calcium glutamate, calcium lactobionate, calcium formate, calcium propionate, calcium ascorbate, and calcium glycerophosphate), calcium polyol phosphates, calcium nitrate, and casein phosphopeptide calcium salt. The water-soluble calcium salt is preferably selected from the group consisting of calcium lactate, calcium acetate, calcium formate, calcium ascorbate, calcium propionate, calcium lactobionate, calcium polyol phosphates, calcium glycerophosphate, casein phosphopeptide calcium salt, calcium chloride, and calcium nitrate.

In a particular embodiment of the present invention, magnesium is used as the alkaline earth metal. When used in the form of a salt, magnesium may be water-soluble, water-insoluble, or poorly water-soluble. A water-soluble magnesium salt is preferred. The term "water-insoluble magnesium salt" as used herein refers to a magnesium salt having a solubility less than 0.1 g/100 ml $H_2O$ in water at 20° C. Examples of water-insoluble magnesium salts include magnesium hydroxide, magnesium carbonate, magnesium fluoride, magnesium silicate, magnesium oxide, magnesium myristate, and magnesium stearate. The term "poorly water-soluble magnesium salt" as used herein refers to a magnesium salt having a solubility of 1 g/100 ml $H_2O$ or more and 5 g/100 ml $H_2O$ or less in water at 20° C. An example of a poorly water-soluble magnesium salt is magnesium oxalate. The term "water-soluble magnesium salt" as used herein refers to a magnesium salt having a solubility higher than 5 g/100 ml $H_2O$ in water at 20° C. The solubility in water at 20° C. of the water-soluble magnesium salt used in the present invention is preferably about 2 wt % or more, more preferably about 3 wt % or more, still more preferably about 4 wt % or more, and particularly preferably about 5 wt % or more. The definition of water-soluble magnesium salts includes a phosphorylated saccharide magnesium salt. As other examples of such water-soluble magnesium salts, the water-soluble magnesium salt is preferably selected from the group consisting of magnesium benzoate, magnesium chloride, magnesium formate, magnesium acetate, magnesium nitrate, magnesium thiosulfate, magnesium hexafluorosilicate, magnesium molybdate, magnesium iodide, magnesium sulfate, magnesium aspartate, and magnesium-L-ascorbyl phosphate.

(Production Method of the Present Invention)

The Composition or Agent of the Present Invention can be Prepared Using any method known in the pertinent field to incorporate therein the following acidic saccharide component containing an alkaline earth metal: (i) an acidic saccharide alkaline earth metal salt such as a phosphorylated saccharide calcium salt; or (ii) a combination of a salt (for example, an alkali metal salt such as a sodium salt) of an acidic saccharide (for example, a phosphorylated saccharide) other than the acidic saccharide alkaline earth metal salt (for example, a phosphorylated saccharide calcium salt) or the acidic saccharide (for example, a phosphorylated saccharide), and an alkaline earth metal salt (for example, calcium chloride) other than the acidic saccharide alkaline earth metal salt (for example, a phosphorylated saccharide calcium salt); or (iii) a mixture of (i) and (ii) above.

In the case of (ii) above, it is preferred to substantially homogeneously incorporate, into the composition or agent of the present invention, the combination of the salt (for example, an alkali metal salt) of the acidic saccharide (for example, a phosphorylated saccharide) other than the acidic saccharide alkaline earth metal salt (for example, a phosphorylated saccharide calcium salt) or the acidic saccharide (for example, a phosphorylated saccharide), and the alkaline earth metal salt (for example, a calcium salt such as calcium chloride) other than the acidic saccharide alkaline earth metal salt (for example, a phosphorylated saccharide calcium salt). The composition or agent homogeneously containing these components has the advantage of being easily produced.

In the case of (ii), a portion containing the salt of the acidic saccharide (for example, a phosphorylated saccharide) or the acidic saccharide (for example, a phosphorylated saccharide) and a portion containing the alkaline earth metal salt (for example, a calcium salt) other than the acidic saccharide alkaline earth metal salt (for example, a phosphorylated saccharide calcium salt) may be separated from each other. In this case, the composition or agent of the present invention should be designed to release the alkaline earth metal salt (for example, a calcium salt) other than the acidic saccharide alkaline earth metal salt (for example, a phosphorylated saccharide calcium salt) simultaneously with or after the release of the salt (for example, an alkali metal salt) of the acidic saccharide (for example, a phosphorylated saccharide) other than the acidic saccharide alkaline earth metal salt (for example, a phosphorylated saccharide calcium salt) or the acidic saccharide (for example, a phosphorylated saccharide). If the alkaline earth metal salt (for example, a calcium salt such as calcium chloride) other than the acidic saccharide alkaline earth metal salt (for example, a phosphorylated saccharide calcium salt) is released earlier than the acidic saccharide (for example, a phosphorylated saccharide) or its salt, the alkaline earth metal ion (for example, a calcium ion) will be precipitated disorderly on the scalp, which is undesirable.

The foregoing applies to all the compositions or agents of the present invention.

(Dosage Forms and Other Components and Active Ingredients)

The composition or agent of the present invention is used in the form of a homogeneous solution, a lotion, a gel, or the like, in accordance with a conventional method, for hair tonics, hair creams, hair styling liquids, shampoos, pomades, conditioners, and the like. The composition or agent of the present invention can also be used as an external preparation having the hair-restoration effect.

The composition or agent of the present invention can take the form of an aerosol composition. In this case, the composition or agent of the present invention can contain, besides the above-described components, lower alcohols such as n-propyl alcohol and isopropyl alcohol; inflammable gases such as butane, propane, isobutane, liquefied petroleum gas, and dimethyl ether; and compressed gases such as nitrogen gas, oxygen gas, carbon dioxide gas, and nitrous oxide gas. The external preparation and agent for hair restoration according to the present invention are used as quasi drugs for skin, for example, and are provided as dosage forms suitable for their usage. Specific examples of dosage forms include, but are not particularly limited to, ointments, liquids, extracts, lotions, tonics, sprays, and emulsions. Such a quasi drug can contain, besides plant extracts, any combination of pharmacologically acceptable carriers such as auxiliary agents, stabilizers, humectants, emulsifiers, absorption enhancers, and surfactants.

The composition or agent of the present invention includes the function of demonstrating a stronger hair-restoration effect and/or an excellent hair-shedding prevention effect, by suppressing the transition of the hair cycle from the anagen phase to the telogen phase, and further prolonging the anagen phase, particularly through the promotion of proliferation of follicle dermal papilla cells. To further enhance this synergistic effect, the composition or agent of the present invention can contain, as required, or depending on the intended use, any optional components and/or other active ingredients besides the acidic saccharide alkaline earth metal salt, without interfering with the purposes and effects of the present invention.

Such optional components and/or other active ingredients can be selected as appropriate depending on the purpose, without particular limitation, and examples include water, ethanol, nonionic surfactants, amphoteric surfactants or other surfactants, celluloses, plant oils, ester oils, keratolytic agents, polymer resins, ultraviolet absorbers, vitamins, amino acids, coloring agents, perfumes, and other active ingredients.

Examples of types of water include purified water, distilled water, ion-exchange water, pure water, ultrapure water, and deep sea water.

Examples of celluloses include hydroxymethylcellulose, hydroxypropylcellulose, and hydroxypropylmethylcellulose.

Examples of nonionic surfactants include sorbitan fatty acid esters (such as sorbitan monolaurate and sorbitan monooleate), polyoxyethylene hydrogenated castor oil, polyoxyethylene hydrogenated castor oil monostearate or isostearate, glycerol fatty acid esters, and polyglycerol fatty acid esters (such as decaglycerol monomyristate and pentaglycerol monomyristate).

Examples of esters include polyhydric alcohol fatty acid esters (polyhydric alcohol fatty acid esters such as glycerol tri-2-ethylhexanoate and trimethylolpropane triisostearate).

Examples of plant oils include *eucalyptus* oil, safflower oil, evening primrose oil, and jojoba oil.

Examples of ester oils include unsaturated fatty acid alkyl esters (such as ethyl oleate and isopropyl linoleate), linoleic acid ester, methyl myristate, and isopropyl myristate.

Examples of polymer resins include amphoteric polymers, cationic polymers, anionic polymers, and nonionic polymers.

Examples of ultraviolet absorbers include octyl methoxycinnamate (Neo Heliopan AV), oxybenzone, and urocanic acid.

Examples of vitamins include vitamin A, vitamin B, vitamin C, vitamin E, tocopherols such as tocopherol acetate, nicotinic acid, methyl nicotinate, benzyl nicotinate, butoxyethyl nicotinate, nicotinate, tocopherol succinate, tocopherol nicotinate, ester of tocopherol and nicotinic acid, inositol hexanicotinate, and tocopherol linoleate. Examples of amino acids include glutamic acid, methionine, serine, glycine, cystine, and threonine.

Furthermore, the agent for hair restoration or the agent for hair growth can contain, as required, other active ingredients besides the active ingredient of the present invention, for example, commonly employed hair-nourishing medicinal agents such as keratolytic agents, hair-follicle activators, cell activators, blood circulation accelerators (vasodilators), antimicrobial agents, anti-inflammatory agents, moisturizers, anti-seborrheic agents, topical stimulants, skin function-enhancing agents, anti-androgen agents, potassium channel openers, and antioxidants, thereby improving the hair-restoration or hair-growth effect. Examples of keratolytic agents include salicylic acid and resorcin. Examples of hair-follicle activators include flavanonols, N-acetyl-L-methionine, pantothenic acid and its derivatives, adenosine and its derivatives, potassium aspartate, glyceride pentadecanoate, 6-b enzylaminopurine, mononitroguaiacol sodium, photosensitizer 301, biotin, *Stephaura cepharantha* extract, *ginseng* extract (such as *Panacis japonici* rhizoma extract or *Panax ginseng* extract), grape extract, apple extract, yeast extract, garlic component, pearl protein extract, placental extract, royal jelly, acetylcholine, *Swertia japonica* extract, iodized garlic extract, ginkgo extract, carpronium chloride, spironolactone, vitamin B6 hydrochloride, γ-oryzanol, circuletin, cromakalim, cepharanthine, nicorandil, vitamin E (such as DL-α-tocopherol, D-α-tocopherol, DL-α-tocopherol acetate, and D-α-tocopherol acetate), nicotinic acids (such as nicotinic acid, DL-α-tocopherol nicotinate, nicotinamide, and benzyl nicotinate), pinacidil, minoxidil, phthalides, *Cinchona* extract, *Acorus calamus* root extract, *Sophora* extract, diisopropylamine dichloroacetate, bitter orange peel extract, *Swertia* herb extract, *capsicum tincture*, *Citrus junos* extract, cantharis tincture, and *Zingiberis* rhizoma tincture. Examples of cell activators include glyceride pentadecanoate, *Coleus forskohlii* extract, *ginseng* extract, and adenosine. Examples of blood circulation accelerators (vasodilators) include carbon dioxide, nicotinamide, benzyl nicotinate, *Swertia japonica* extract, *ginseng* extract, carpronium chloride, minoxidil, cepharanthine, nonanoic acid vanillylamide, vitamin E and its derivatives. Examples of antimicrobial agents include isopropylmethylphenol, benzalkonium chloride, Octopirox, zinc pyrithione, and hinokitiol. Examples of anti-inflammatory agents include licorice extract, glycyrrhizic acid and its derivatives, glycyrrhetic acid and its derivatives, azulene, guaiazulene, *Scutellaria* root extract, chamomile extract, *Sasa veitchii* extract, rosemary extract, *perilla* extract, white birch extract, mallow extract, peach leaf extract, and *Achillea millefolium* extract. Examples of moisturizers include St. John's wort extract, oats extract, glycerol, *polyanthes tuberosa* polysaccharide, plant worm extract, *Isodonis herba* extract, barley extract, grape extract, propylene glycol, *Platycodon grandiflorum* extract, and *coix* seed extract. Examples of anti-seborrheic agents include sulfur, lecithin, *Polygonum multiflorum* root extract, and thioxolone. Examples of topical stimulants include camphor and *capsicum tincture*. Examples of skin function-enhancing agents include panthenol derivatives such as D-panthenol and pantothenyl ethyl ether. Examples of anti-androgen agents include cyproterone acetate, 11 α-hydroxyprogesterone, flutamide, 3-deoxyadenosine, chlormadinone acetate, ethinylestradiol, spironolactone, episterone, finasteride, aloe, Japanese pepper, clove extract, cuachalalate extract, and *Panax ginseng*. Examples of potassium channel openers include minoxidil, cromakalim, diazoxide and derivatives thereof, and pinacidil. Examples of antioxidants include *Camellia sinensis* extract, tea extract, *Rosa multiflora* fruit extract, *kohki* extract, vitamin C and its derivatives, erythorbic acid, propyl gallate, and dibutylhydroxytoluene. Examples of other useful components include orizanol, dextran sulfate sodium, acetylcholine, *Swertia japonica* extract, *capsicum tincture*, cantharides tincture, *Zingiberis* rhizoma tincture, *Panax ginseng, Panacis japonici* rhizoma, cepharanthine, circuletin, nicorandil, pinacidil, garlic extract, *Angelica sinensis* extract, *Gentiana* extract, iodized garlic extract, liquorice, minoxidil, *Cnidium* rhizome extract, *Panacis* japonici rhizoma, ginger, *Rehmannia* root, aloe, spironolactone, hinokitiol, hinokiol, *Panax ginseng*, peach kernel, *Stephaura cepharantha, Sinomenium* stem, *Psoralea corylifolia, Astragalus* root, safflower, hydrolyzed sugar-processed *ginseng* extract (hydrolyzed *Codonopsis pilosula* root extract), hydrolyzed black soybean extract, *Bletilla striata* extract, Pau d'arco bark extract (*Tabebuia impetiginosa* bark extract), soybean milk fermented liquid, hibiscus flower fermented liquid, *Salicornia europaea* extract, dylily flower fermented liquid (fermented liquid of a flower in the genus *Hemerocallis*), *Callicarpa japonica* extract, chamomile extract, extracts of seaweeds such as *Laminariaceae Bory*, extracts of marine flowering plants such as *Zostera marina*, linoleic acid and its derivatives or its processed products (for example, liposomal linoleic acid), 2,5-dihydroxybenzoic acid derivatives, collagen of animal or fish origin or its derivatives, elastin or its derivatives, nicotinic acid and its derivatives, glycyrrhizic acid and its derivatives (such as a dipotassium salt (glycyrrhizinate dipotassium)), t-cycloamino acid derivatives, vitamin A and its derivatives, vitamin C and its derivatives, allantoin, α-hydroxy acids, diisopropylamine dichloroacetate, γ-amino-β-hydroxybutyric acid, bis-alkaloids derived from *Stephaura cepharantha*, herbal medicine extracts such as *Gentiana* extract, licorice extract, Job's tears extract, *ginseng* extract, and aloe extract, rice extract or its hydrolysate, extracts of pigmented rices (such as black rice, red rice, purple rice, and green rice) or their hydrolysates, rice bran extract or its hydrolysate, fermented rice extract, *Ulva pertusa* extract, mulberry bark extract, and *Zizyphus joazeiro* extract.

The following components for preparations can also be incorporated, besides the components of the present invention, without interfering with the effects of the present invention: minoxidil, diphenhydramine hydrochloride, antihistamines such as isopenzyl hydrochloride; anti-inflammatory agents such as glycyrrhetic acid and guaiazulene; urea, keratolytic agents such as salicylic acid; antibacterial agents such as chlorhexidine gluconate, isopropylmethylphenol, quarternary ammonium salts, hinokitiol, and piroctone olamine; moisturizers such as sodium hyaluronate, glycerol, and chondroitin sulfate; animal and plant extracts such as yew tree, moutan bark, liquorice, St. John's wort, aconite, *Eriobotrya japonica, Artemisia capillaris*, comfrey, *angelica*, saffron, *Gardenia* fruit, rosemary, sage, *Saussurea lappa, Aristolochia debilis*, hop, and placenta extracts; vitamins such as retinol acetate, pyridoxine hydrochloride, ascorbic acid, thiamine nitrate, cyanocobalamin, biotin, and tocopherol acetate; oils such as squalane, liquid paraffin, and lecithin; surfactants such as polyoxyethylene hydrogenated castor oil; essential oil components such as menthol and camphor; antioxidants such as dibutylhydroxytoluene and isopropyl gallate; metal-ion sequestrants such as ethylenediaminetetraacetate or its salts; dyes; and perfumes.

A blood flow-promoting component is a component for improving the flow of blood that leads to follicle dermal papilla cells and hair matrix cells, and activates the cellular metabolism by efficiently supplying oxygen and nutrients necessary for the growth of hair. Such a blood flow-promoting component, therefore, can be used in combination with the components of the present invention. Examples of such blood flow-promoting components include vitamin E, vitamin E derivatives such as tocopherol acetate, nicotinic acid and nicotinic acid derivatives such as nicotinamide and benzyl nicotinate, cepharanthine, carpronium chloride, acetylcholine, γ-oryzanol, circuletin, cromakalim, nicorandil, pinacidil, phthalides, dialkylmonoamine derivatives, ginkgo extract, chamomile extract, *Angelica sinensis* extract, *Cnidium* rhizome extract, rosemary extract, watercress extract, safflower extract, *capsicum tincture, Citrus unshiu* peel extract, *Zingiberis* rhizoma tincture, *ginseng* extract, *Acorus calamus* root extract, *Tilia japonica* extract, *Isodonis herba* extract, *Swertia* herb extract, *Tilia cordata* flower extract, grape seed extract, *Swertia japonica* extract, and *Citrus junos* extract.

The above-mentioned active ingredients can also be used for cosmetic products. In this case, examples of dosage forms include, but are not particularly limited to, water-in-oil or oil-in-water emulsion cosmetic products, creams, lotions, gels, foams, essences, foundations, packs, sticks, and powders. Such cosmetic products can contain, besides plant extracts, any combination of commonly employed cosmetic components, such as oils, surfactants, ultraviolet absorbers, alcohols, chelating agents, pH adjusters, preservatives, thickeners, dyes, perfumes, and various skin nutrients. Specifically, medicinal components to be incorporated into cosmetic products for skin can be added and incorporated, for example, ultraviolet absorbers such as particulate zinc oxide, titanium oxide, Parsol MCX, and Parsol 1789; vitamins such as ascorbic acid; moisturizers such as sodium hyaluronate, petrolatum, glycerol, and urea; hormonal agents and other skin-whitening components such as kojic acid, arbutin, placental extract, and rucinol; steroidal agents; inhibitors (indomethacin, ibuprofen) for production and release of chemical mediators represented by arachidonic acid metabolites and histamine; anti-inflammatory agents such as receptor antagonists; anti-androgen agents; sebum secretion inhibitors such as vitamin A acid, royal jelly extract, and royal jelly acid; peripheral vasodilators such as tocopherol nicotinate, alprostadil, isoxsuprine hydrochloride, and tolazoline hydrochloride as well as carbon dioxide gas and the like having peripheral vasodilator action; blood circulation accelerators such as minoxidil, carpronium chloride, *capsicum tincture*, vitamin E derivatives, ginkgo extract, and *Swertia japonica* extract; cell activators such as glyceride pentadecanoate and nicotinamide; antibacterial agents such as hinokitiol, L-menthol, and isopropylmethylphenol; agents such as glycyrrhizic acid and its derivatives or its salts; and ceramides and ceramide analog compounds.

When the acidic saccharide alkaline earth metal salt of the present invention is used for a pharmaceutical product, a quasi drug, or a cosmetic product, the amount of the acidic saccharide alkaline earth metal salt incorporated therein is generally 0.00001 to 5 wt %, particularly 0.01 to 2 wt %, preferably 0.1 to 1 wt %, and more preferably 0.2 to 0.5 wt % or 0.2 to 0.4 wt %, calculated in terms of dry matter, based on the entire composition of the pharmaceutical product, quasi drug, or cosmetic product. The amount of the acidic saccharide alkaline earth metal salt, however, is not limited thereto, and a person skilled in the art can determine an appropriate concentration at which the hair-restoration effect or hair-growth effect is observed. In particular, with POs-Ca (R), such an effect is observed at a concentration of 0.0625 to 1.0 wt %, and the concentration is particularly 0.01 to 2 wt %, preferably 0.1 to 1 wt %, and more preferably 0.2 to 0.5 wt % or 0.2 to 0.4 wt %. In an alternative embodiment, it is to be understood that the concentration of POs-Ca (R) is preferably 0.2 wt % or more, or more than 0.2 wt %, or 0.2 to 1.0 wt %, over 0.2 to 1.0 wt %, 0.3 wt % or more, or 0.3 to 1.0 wt %. It is also to be understood that when POs-Ca (R) is provided as a combination of POs-Na and calcium chloride, the hair-restoration effect or hair-growth effect can be demonstrated at a lower concentration. For example, the concentration can be 0.1 wt % or more, or 0.1 to 0.8 wt %, or may be 0.8 wt % or less. Alternatively, the concentration may be less than 1.0 wt %, or 0.1 wt % or more and less than 1.0 wt %. On the other hand, with glucose-1-phosphate calcium, a preferred range of concentrations at which the hair-restoration effect or hair-growth effect can be demonstrated may be more than 0.3 wt % and less than 1.0 wt %, for example, more than 0.3 wt % and 0.8 wt % or less, or 0.6 wt % or more and less than 1.0 wt %, or 0.6 to 0.8 wt %, without being limited thereto.

Furthermore, when the above-mentioned active ingredients are used for a cosmetic product, a pharmaceutical product, or a quasi drug, the following components can be used in appropriate combinations, as required: powders such as chalk, talc, fuller's earth, kaolin, starch, rubber, colloidal silica, and sodium polyacrylate; oils or oily substances such as mineral oils, plant oils, and silicone oils; emulsifiers such as sorbitan trioleate, sorbitan tristearate, glycerol monooleate, and polymeric silicone surfactants; preservatives such as para-hydroxybenzoate esters; antioxidants such as butylated hydroxytoluene; humectants such as glycerol, sorbitol, 2-pyrrolidone-5-carboxylate, dibutyl phthalate, gelatin, and polyethylene glycol; buffers such as a lactate with a base, for example, triethanolamine or sodium hydroxide; surfactants such as glycerol fatty acid esters, sorbitan fatty acid esters, sucrose fatty acid esters, and alkyl glucosides; waxes such as bees wax, ozokerite wax, and paraffin wax; thickeners; activity enhancers; colorants; and perfumes.

Additional components are not limited to those mentioned above, as long as they are any of various components having hair-restoration, hair-growth, hair-nourishment, and hair-increasing effects that may be contained in addition to the acidic saccharide alkaline earth metal salt. That is, the foregoing is merely a list of examples of possible active ingredients. Thus, a variety of agents having hair-restoration, hair-growth, hair-nourishment, and hair-increasing effects can be incorporated as active ingredients, such as antibacterial agents, anti-androgen agents, sebum secretion inhibitors, immunosuppressive agents, antihistamines, topical stimulants, keratin-softening agents, and anti-apoptotic agents, without interfering with the safety of the body, for example.

The agent for hair restoration according to the present invention in actual use adopts dosage forms that can be applied or sprayed to the hair or scalp (such as liquids, emulsions, creams, gels, stick pomades, shampoos, sprays, mousses, packs). Thus, water, lower alcohols (such as methanol, ethanol, 1-propanol, 2-propanol, 1-butanol, and 2-butanol), polyhydric alcohols (such as ethylene glycol, diethylene glycol, triethylene glycol, polyethylene glycol, propylene glycol, dipropylene glycol, polypropylene glycol, 1,3-butylene glycol, and isoprene glycol), acetonitrile, esters (such as ethyl acetate and butyl acetate), hydrocarbons (such as hexane, heptane, and liquid paraffin), ethers (such as ethyl ether and propyl ether), perfumes, preservatives, antioxidants, ultraviolet absorbers, dyes, perfumes, and the like may be incorporated as appropriate, without interfering with the effects of the present invention.

Any components that have already been shown to have the hair-restoration effect and/or hair-growth effect in the pertinent field may be used as other active ingredients for use in the present invention. As such other components having the hair-restoration effect or hair-growth effect, those found in "Guidelines for the Treatment of Alopecia" by the Japanese Dermatological Association may be used, including those mentioned above, such as a chondroitin sulfate proteoglycan (known as versican), minoxidil, finasteride, adenosine, carpronium chloride, t-flavanone, 6-benzylaminopurine (cytopurine), pentadecane, ketoconazole, and cepharanthine. As will be shown in the Examples, the agent of the present invention is believed to demonstrate at least an additive effect in conjunction with minoxidil. The effects of the present invention, therefore, are believed to generally have additional action to other components.

(Administration)

For administration of the agent of the present invention to a subject, various delivery systems are known, and, using such a system, the agent of the present invention can be directly administered to an appropriate site (for example, the scalp). Such a system is provided by, for example, dissolving or suspending the agent of the present invention into an aqueous or non-aqueous medium; encapsulating the agent of the present invention into a liposome, a microparticle, or a microcapsule; or using receptor-mediated endocytosis. Examples of modes of administration include, but are not limited to, percutaneous, intracutaneous, intramuscular, intraabdominal, intravenous, subcutaneous, intranasal, extradural, and oral routes. The pharmaceutical product can be administered via a suitable route, for example, via injection, or via a bolus injection, through absorption via the epithelial or mucocutaneous lining (for example, the oral cavity, rectal, or intestinal mucosa). Moreover, an inhaler or an atomizer can be used through the use of an aerosolizer, as required. Furthermore, the pharmaceutical product can be administered in conjunction with other biological activators. The administration can be either systemic or topical.

(General Techniques)

The molecular biological techniques, biochemical techniques, and microbiological techniques used herein are those that are well known and conventionally used in the pertinent field, and are described in, for example, Sambrook J. et al. (1989). Molecular Cloning: A Laboratory Manual, Cold Spring Harbor, 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press; and *Bessatsu Jikken Igaku "Idenshi Dounyu & Hatsugen Kaiseki Jikken Hou"* (Supplementary Volume, Experimental Medicine "Gene Transfer & Expression Analysis Experimental Methods"), Yodosha, 1997. These documents are incorporated herein by reference in sections relevant to the present specification (possibly in their entirety).

The reference documents such as scientific documents, patents, and patent applications cited herein are incorporated herein by reference in their entirety as if individually specifically described.

The present invention has been described above with reference to preferred embodiments for easy understanding. The present invention will be hereinafter described based on examples; however, the foregoing description and the following examples are provided solely for illustrative purposes, rather than for limiting the present invention. The scope of the present invention, therefore, is not limited by the embodiments or examples specifically described herein, but is limited only by the claims.

EXAMPLES

Examples of the present invention will be hereinafter described. Biological samples or the like were handled in compliance with the standards specified by the Ministry of Health, Labor and Welfare, the Ministry of Education, Culture, Sports, Science and Technology, or the like, where appropriate.

Production Example: Phosphorylated Saccharide Calcium Salt Used

The phosphorylated saccharide calcium (POs-Ca (R)) used in the following experiments can be prepared from potato starch in accordance with the procedures described in Example 1 of JP H08-104696 A, using calcium chloride instead of sodium chloride. Specifically, the phosphorylated saccharide calcium is a phosphorylated saccharide calcium mixture in which calcium is bound to each of phosphorylated saccharides in which one or two phosphate groups are bound within the molecule of an oligosaccharide composed of 2 to 8 glucose residues bound by α-1,4 linkages. This phosphorylated saccharide calcium is a mixture of phosphorylated saccharide calcium in which one phosphate group is bound within the molecule of an oligosaccharide composed of 3, 4, or 5 glucose residues, and calcium is bound to this phosphate group, and phosphorylated saccharide calcium in which two phosphate groups are bound within the molecule of an oligosaccharide composed of 5, 6, 7, or 8 glucose residues, and calcium is bound to these phosphate groups. Here, the molar ratio of the phosphorylated saccharide calcium in which one phosphate group is bound, relative to the phosphorylated saccharide calcium in which two phosphate groups are bound, is about 8:2. In the following experiments, the salt thus prepared was used. Besides using the present method utilizing an ion-exchange resin, various metal salts of phosphorylated saccharides can be easily prepared using general electrodialysis, by adding various metal salts after desalting. As the calcium salt of phosphorylated saccharides, a product sold as phosphorylated oligosaccharide calcium by Ezaki Glico Co., Ltd. can also be suitably used.

(General Technique)

Hair-related experiments according to the present invention will be hereinafter described.

(Materials and Method)

The reagents and method employed in the present invention will be described first.

(1) General Reagents Special-grade sodium hydroxide, calcium chloride dihydrate, and magnesium chloride hexahydrate from Wako Pure Chemical Industries, Ltd. were used.

(2) Water

As water, deionized water produced using the MilliQ (Merck Millipore, US) was used.

(3) 10% (w/v) Aqueous Solution of POs-Ca (R)

1.0 g of POs-Ca (R) (containing 5.0% (w/w) calcium; Oji Cornstarch Co., Ltd.) was dissolved in 8 ml of water, and adjusted to pH 7.2 with 1 M NaOH, using a hand-held pH meter (LAQUAtwin B-711, Horiba, Ltd.). The solution was diluted to 10 ml in a measuring cylinder, and sterilized by being passed through a 0.20-μm filter (Minisart, surfactant-free cellulose acetate; Sartorius Stedim Biotech, US) with a 10-ml syringe (Terumo Corporation).

(4) 1.84% (w/v) Aqueous Solution of $CaCl_2 \cdot 2H_2O$

An aqueous solution containing an equivalent amount of calcium to that of 10% POs-Ca (R) was used to compare the influence of calcium. This solution was prepared by dissolving 0.184 g of $CaCl_2 \cdot 2H_2O$ in water to give a volume of 10 ml, and then sterilizing the solution by passing through a 0.22-μm filter with a syringe.

(5) 10% (w/v) Aqueous Solution of POs-Na 1.0 g of POs-Na (Oji Cornstarch Co., Ltd.) was dissolved in 8 ml of water, and adjusted to pH 7.2 with 1 M NaOH, using a hand-held pH meter (LAQUAtwin B-711, Horiba, Ltd.). The solution was diluted to 10 ml in a measuring cylinder, and sterilized by being passed through a 0.20-μm filter (Minisart, surfactant-free cellulose acetate; Sartorius Stedim Biotech, US) with a 10-ml syringe (Terumo Corporation).

(6) 10% (w/v) Aqueous Solution of POs-Mg 1.0 g of POs-Mg (containing 5.6% (w/w) magnesium; Oji Cornstarch Co., Ltd.) was dissolved in 8 ml of water, and adjusted to pH 7.2 with 1 M NaOH, using a hand-held pH meter (LAQUAtwin B-711, Horiba, Ltd.). The solution was diluted to 10 ml in a measuring cylinder, and sterilized by being passed through a 0.20-μm filter (Minisart, surfactant-free cellulose acetate; Sartorius Stedim Biotech, US) with a 10-ml syringe (Terumo Corporation).

(7) 4.45% (w/v) Aqueous Solution of $MgCl_2 \cdot 6H_2O$

An aqueous solution containing an equivalent amount of magnesium to that of 10% POs-Mg was used to compare the influence of magnesium. This solution was prepared by dissolving 0.445 g of $MgCl_2 \cdot 6H_2O$ in water to give a volume of 10 ml, and then sterilizing the solution by passing through a 0.22-μm filter with a syringe.

(8) 12.9% (w/v) Aqueous Solution of G1P-Ca

An aqueous solution of glucose-1-phosphate was neutralized by adding calcium hydroxide and dried, thus preparing a salt having a calcium content of 3.8% (w/w). 0.129 g of the salt was weighed out and dissolved in 9 ml of water. The aqueous solution was adjusted to pH 7.2 with 1 M NaOH, using the hand-held pH meter. The solution was diluted to 10 ml in a measuring cylinder, and sterilized by being passed through a 0.20-μm filter (Minisart, surfactant-free cellulose acetate; Sartorius Stedim Biotech, US) with a 10-ml syringe (Terumo Corporation).

(9) Human Follicle Dermal Papilla Cells

A strain (Lot. 3092504.12) sold by PromoCell (Germany) was used as human follicle dermal papilla cells. The cells were cultured in a $CO_2$ incubator at 37° C., using a special medium for follicle dermal papilla cells (PromoCell), unless otherwise indicated. Cell subculturing was performed as follows: cells were seeded at 5000 to 10000 cells/cm$^2$ in an uncoated dish, and when the cells reached subconfluent, they were treated with trypsin-EDTA (0.03%) and detached, and then re-seeded. The trypsin-EDTA treatment allows complete detachment of the cells by incubation at 37° C. for nearly 10 minutes, with a high survival rate. The medium was replaced about once every 3 days.

Example 1: Comparison of Cell Proliferation Rate Between Substances of Different Calcium Species In this example, the cell proliferation rate was compared between substances of different calcium species. Specific procedures are described below.

(1) Human follicle dermal papilla cells were seeded in a 96-well collagen I-coated plate (BD Biocoat Collagen I 96-well clear plate) at $1.6 \times 10^3$ cells/well and cultured at 37° C. for 24 hours. Cells were not seeded in two wells on the plate for blanks.

(2) Solutions of the compositions shown in the table were prepared in a concentration series starting from a 10% (w/v) aqueous solution of POs-Ca (R), a 1.84% (w/v) aqueous solution of $CaCl_2 \cdot 2H_2O$, or a 12.9% (w/v) aqueous solution of G1P-Ca.

(3) The above-described aqueous solutions and the special medium were mixed at a ratio of 1:9 to prepare media having five different concentrations for each calcium species with a final concentration of 1/10 shown in Table 1. The media in each of the columns of Table 1 have the same calcium concentration.

(4) The medium was removed from the plate in (2) and then replaced by the media obtained in (3). For each of the media having each concentration, five wells (five samples) were provided as an experimental section. As a control, a medium was prepared by mixing water and the special medium at a ratio of 1:9, and the medium in five wells was replaced by this medium.

(5) The above-described plate was cultured at 37° C. for 3 days.

(6) To each well, 20 μl of a solution prepared by diluting Premix WST-1 cell proliferation assay system (Takara) with an equivalent volume of the special medium was added, and the color reaction was performed for 30 minutes.

(7) Absorbance at 440 nm was measured for each well, using a fluorescence microplate reader (Varioskan Flash 2.4; Thermo Fisher Scientific, US).

(8) The value obtained by subtracting the absorbance of the blank wells from the absorbance of the well of the sample was defined as the value of the relative amount of cells of the sample in each well. The degree of cell proliferation relative to the control was calculated by dividing the value of the relative amount of cells in each well, by the average value of the relative amount of cells in the control medium.

TABLE 1

Sample Solutions for Addition Used in the Preparation of Media in Example 1

| Concentration Series | 1 x | ½ x | ¼ x | ⅛ x | 1/16 x |
|---|---|---|---|---|---|
| POs—Ca (R) (% w/v) | 10 | 5.0 | 2.5 | 0.125 | 0.0625 |
| $CaCl_2$ (% w/v) | 1.84 | 0.92 | 0.46 | 0.23 | 0.115 |

(x represents the factor.)

(Results)

The results are shown in FIG. 1A. As shown in the graph, the maximum proliferation rate was demonstrated when 0.25% POs-Ca (R) was added, and follicle dermal papilla cells proliferated significantly more than those with calcium chloride and the control (POs-Ca (R) showed a 66.0% increase relative to the control, whereas calcium chloride showed a 5.6% increase relative to the control). Furthermore, at all tested concentrations of 0.0625%, 0.12%, 0.25%, 0.5%, and 1.0% of POs-Ca (R), proliferation rates higher than those with calcium chloride (at 0.0115%, 0.023%, 0.046%, 0.092%, and 0.184% (each calculated to be the same as the corresponding concentration of POs-Ca (R) in terms of the amount of calcium)) were demonstrated. In particular, at concentrations of 0.0115% and 0.023% of calcium chloride, the proliferation rate tended to decrease, whereas at corresponding concentrations of 0.0625% and 0.12% of POs-Ca (R), the proliferation rate tended to increase. At concentrations of 0.092% and 0.184% of calcium chloride, the proliferation rate tended to increase, and similarly at corresponding concentrations (0.5% and 1.0%) of POs-Ca (R), the proliferation rate demonstrated a 50% to at least a 2-fold increase.

Example 2: Experiment for Comparing Cell Proliferation Rate Between Substances of Different Calcium Species (2)

1. The procedures (1) and (3) to (5) in Example 1 were performed in the same manner as described above. Solutions of the compositions shown in the following table were prepared in a concentration series starting from a 10% (w/v) aqueous solution of POs-Ca (R), a 12.9% (w/v) aqueous solution of G1P-Ca, a 1.84% (w/v) aqueous solution of $CaCl_2 \cdot 2H_2O$, or a 10% (w/v) aqueous solution of POs-Na.

TABLE 1A

| | Concentration Series | | | | | | |
|---|---|---|---|---|---|---|---|
| | 1 x | 0.8 x | 0.6 x | 0.4 x | 0.3 x | 0.2 x | 0.1 x |
| POs-Ca (R) (% w/v) | 10 | 8.0 | 6.0 | — | 3.0 | 2.0 | 1.0 |
| $CaCl_2$ (% w/v) | 1.84 | 1.47 | 1.10 | 0.74 | 0.12 | 0.37 | 0.18 |
| POs-Na (% w/v) | 10 | 8.0 | 6.0 | 4.0 | 3.0 | 2.0 | 1.0 |
| G1P-Ca (% w/v) | 12.9 | 10.3 | 7.74 | — | 3.87 | 2.58 | 1.29 |
| POs-Na + $CaCl_2$ | A mixture of POs-Na and $CaCl_2$ having a corresponding concentration in each column. | | | | | | |

(x represents the factor.)

2. In place of the conditions ((6), (7) and (8)) in Example 1, Cell Counting Kit-F (Dojindo Molecular Technologies, Inc.) was added to each well in accordance with the manual, and the number of cells was counted.

Figure 1B:
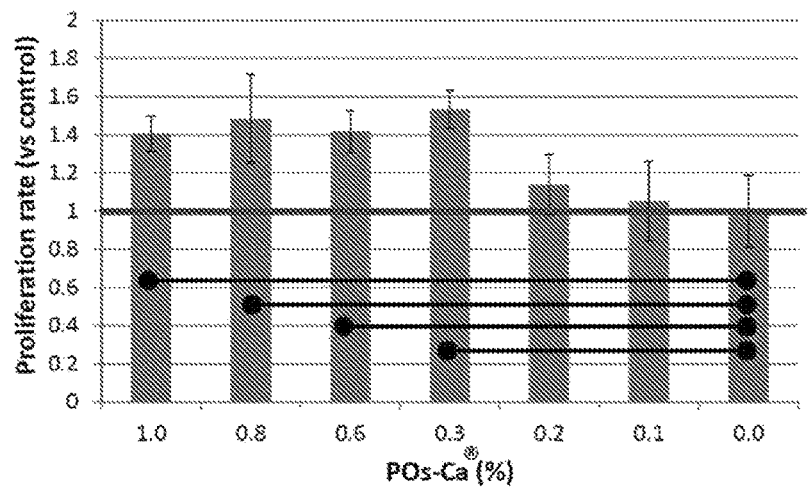
FIG. 1B shows the results of follicle dermal papilla cell proliferation tests performed using POs-Ca (R) in separate lots. The results indicated that concentrations over 0.2% of POs-Ca (R) have the effect of proliferating follicle dermal papilla cells, as working concentrations. Means±standard deviations are shown, and $p<0.05$, Dunnett's test, is shown by the lines each connecting black circles.
Figure 1C:
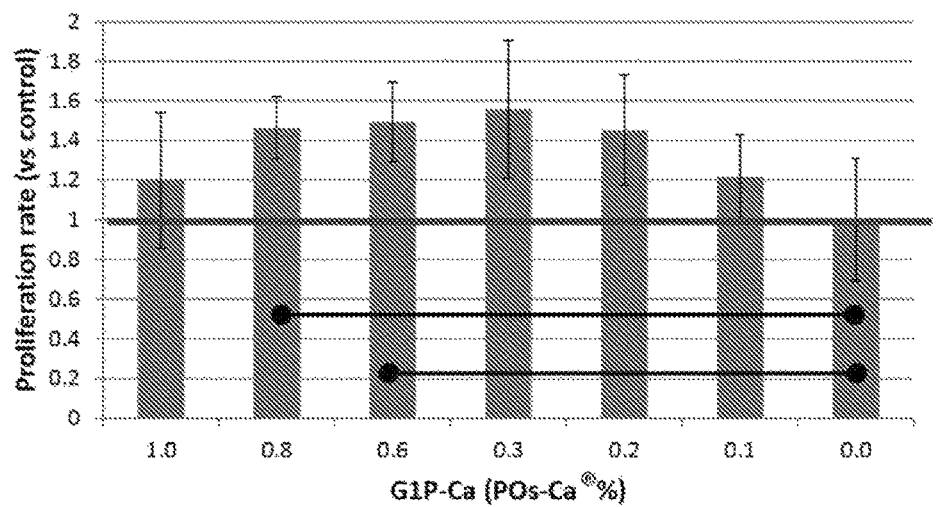
FIG. 1C shows the results of follicle dermal papilla cell proliferation tests performed using glucose-1-phosphate calcium in separate lots. The results indicated that concentrations over 0.3% of glucose-1-phosphate calcium have the effect of proliferating follicle dermal papilla cells, as working concentrations. Means±standard deviations are shown, and $p<0.05$, Dunnett's test, is shown by the lines each connecting black circles.

3. (Results) As shown in FIGS. 1B to 1D, POs-Ca (R) allowed the number of follicle dermal papilla cells to significantly increase at concentrations over 0.2-fold. G1P-Ca exhibited a similar tendency, and allowed the number of cells to significantly increase at 0.6- to 0.8-fold concentrations. The combination of POs-Na and $CaCl_2$ also exhibited a similar tendency, and allowed the number of cells to significantly increase at 0.1- to 0.8-fold concentrations. With all of POs-Ca (R), G1P-Ca, and the combination of POs-Na and $CaCl_2$, the number of cells increased at all concentrations, compared to that without addition. Thus, the effect of promoting the proliferation of follicle dermal papilla cells can be expected by the inclusion of POs-Ca (R), G1P-Ca, and the combination of POs-Na and $CaCl_2$ preferably at 0.6- to 0.8-fold concentrations.

In contrast, as shown in FIG. 1E, when $CaCl_2$ or POs-Na was used alone, an increase in the number of cells was not observed compared to that without addition. This showed that both the acidic saccharide component and calcium component are essentially required for the proliferation of follicle dermal papilla cells.

Example 3: Expression of Various Genes Related to the Hair-Restoration Effect and Hair-Growth Effect Next, in this example, changes in the expression of various genes induced by the component of the present invention were examined.

CSPG4, Wnt5a, ALPL, tenascin C, versican, fibronectin, VEGF, and FGF-7, as well as VEGFB as a negative control were used.

Each of these genes can be explained as follows: Suppression of follicle dermal papilla cell apoptosis is demonstrated by the promotion of the expression of Wnt5a. Hair-follicle angiogenesis is demonstrated by the expression of VEGF. Promotion of hair matrix cell proliferation is demonstrated by the expression of FGF-7. Promotion of the activity of follicle dermal papilla cells is demonstrated by the promotion of the expression of ALPL and versican. Versican is an extracellular matrix specific to follicle dermal papilla cells. Promotion of anagen-phase hair follicles is demonstrated by the expression of tenascin C. Promotion of anagen-phase hair follicles is demonstrated by an increase in the expression of CSPG4. Fibronectin is an extracellular matrix that is extensively present, and is expected to promote follicle dermal papilla cells and the like. Through the upregulation of these genes, follicle dermal papilla cells demonstrate the function of hair-growth phase to promote hair growth. Suppression of the expression of VEGFB, which is upregulated when general calcium agents are administered, leads to the hair-restoration or hair-growth effect.

(Materials and Method)

(1) 500 µl of a special medium in which $4 \times 10^4$ cells/ml of follicle dermal papilla cells were suspended was dispensed into a type I collagen-coated 24-well cell culture plate (Corning), and cultured at a cell density of $1.0 \times 10^4$ cells/cm² at 37° C. for 42 hours. (2) (a) Water (control), (b) a 2.5% (w/v) aqueous solution of POs-Ca (R), and (c) a 0.457% aqueous solution of $CaCl_2$ (having an equivalent amount of calcium to that of (b)) were prepared. Each of the solutions (a) to (c) was mixed with DMEM high glucose (Sigma, USA) at a ratio of 1:9.

(3) The medium was aspirated from each well obtained in (1), the well was washed by adding 1 ml of 1×PBS (137 mM NaCl, 8.1 mM $Na_2HPO_4$, 2.68 mM KCl, 1.47 mM $KH_2PO_4$ (pH 7.4); Wako Pure Chemical Industries, Ltd.), and aspirating the PBS, 500 µl of DMEM high glucose was added, and the cells were incubated in a $CO_2$ incubator at 37° C. for 5 hours. Six wells (six samples) were used as experimental samples for each of the control, POs-Ca (R), and $CaCl_2$.

(4) The medium was removed from each well, and then mRNA was extracted using CellAmp Direct RNA Prep Kit for RT-PCR (Takara). The method was performed in accordance with the manual for the kit.

(5) 8 µl of the extracted mRNA solution (200 µl for each well) was used, and cDNA was obtained by the reverse transcription reaction at a scale of 40 µl, using PrimeScript RT Master Mix (Takara). The reaction conditions were as set forth in the manual for the kit.

(6) 0.5 µl of each of cDNA solutions diluted 2-fold with water, 1 µl of a solution containing 4 µM of each of primers 1 and 2 for each of the genes shown in Table 2, 5 µl of SYBR Premix Ex Taq II (Takara), and 3.5 µl of water were added, and quantitative PCR was performed on each of the genes. Using CFX96 Touch (BIO-RAD, USA), denaturation treatment at 95° C. for 30 seconds was performed, and then a two-step cycle at 95° C. for 5 seconds and at 62° C. for 20 seconds was performed for 65 cycles. Fluorescence intensity after each cycle was measured.

(7) Using PGK1 and GAPDH as reference genes, a comparative analysis of expression levels was performed with the analysis software (Bio-Rad CFX Manager 3.0) included in CFX96Touch. Relative expression levels were calculated under the default conditions of the software.

(8) The average value of calculated expression levels was determined for the six samples derived from the cells treated under the respective conditions, and defined as the expression level relative to the control.

TABLE 2

Primer Sets Used in Quantitative PCR
Table 2 Sequence Information

| Gene | NCBI Gene Name | NCBI Gene ID | Primer 1 (Forward) | Primer 2 (Reverse) |
|---|---|---|---|---|
| Fibronectin | FN1 | 2335 | CCCATCAGCAGGAACACCTT (SEQ ID NO: 1) | GGCTCACTGCAAAGACTTTGAA (SEQ ID NO: 2) |
| CSPG4 | CSPG4 | 1464 | AGCTAGCCAGGACTGATGGA (SEQ ID NO: 3) | CAGCCTAACCTGCTCCAAAG (SEQ ID NO: 4) |
| Tenascin C | TNC | 3371 | AGGGACCACTGGGTGAGAGA (SEQ ID NO: 5) | GGGCTGGTTGTATTGATGCTTT (SEQ ID NO: 6) |
| Versican | VCAN | 1462 | CAAGCATCCTGTCTCACGAA (SEQ ID NO: 7) | CAACGGAAGTCATGCTCAAA (SEQ ID NO: 8) |
| ALPL | ALPL | 249 | GACCCTTGACCCCCACAAT (SEQ ID NO: 9) | GCTCGACTGCATGTCCCCT (SEQ ID NO: 10) |
| Wnt5a | WNT5A | 7474 | AGGGCTCCTACGAGAGTGCT (SEQ ID NO: 11) | GACACCCCATGGCACTTG (SEQ ID NO: 12) |
| VEGF | VEGFA | 7422 | CTACCTCCACCATGCCAAGT (SEQ ID NO: 13) | AGCTGCGCTGATAGACATCC (SEQ ID NO: 14) |
| VEGFB | VEGFB | 7423 | GCAGATCCTCATGATCCGGT (SEQ ID NO: 15) | GGCTTCACAGCACTGTCCTT (SEQ ID NO: 16) |
| FGF-7 | FGF7 | 2252 | TGTCGAACACAGTGGTACCTG (SEQ ID NO: 17) | CCCTTTGATTGCCACAATTC (SEQ ID NO: 18) |
| PGK1 | PGK1 | 5230 | AGGGAAAAGATGCTTCTGGG (SEQ ID NO: 19) | AAGTGAAGCTCGGAAAGCTTCTAT (SEQ ID NO: 20) |
| GAPDH | GAPDH | 2597 | ACAGTCAGCCGCATCTTCTT (SEQ ID NO: 21) | ACGACCAAATCCGTTGACTC (SEQ ID NO: 22) |

(Results)

Figure 2:
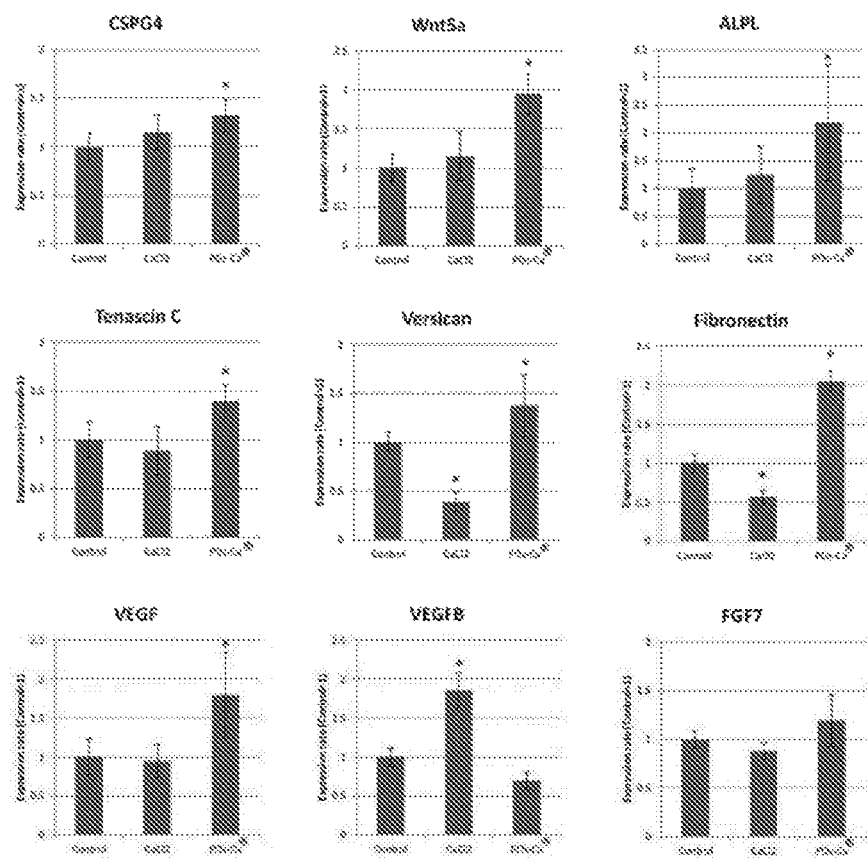
FIG. 2 shows the expression of various genes related to the hair-restoration effect and hair-growth effect. In each graph, the bars show the control, $CaCl_2$, and POs-Ca (R) from the left. The control was taken as 1. The graphs in the upper section show CSPG4, Wnt5a, and ALPL from the left, the graphs in the middle section show tenascin C, versican, and fibronectin from the left, and the graphs in the lower section show VEGF, VEGFB, and FGF7 from the left. Means±standard deviations are shown, and $p<0.05$, Dunnett's test, is shown by *.

The results are shown in FIG. 2. The POs-Ca (R) treatment promoted the expression of the CSPG4, Wnt5a, ALPL, tenascin C, versican, fibronectin, VEGF, and FGF-7 genes more than the control treatment and the $CaCl_2$ treatment. In particular, the expression of the CSPG4, Wnt5a, ALPL, tenascin C, versican, fibronectin, and VEGF genes was significantly increased, compared to that with the control, in the Dunnett multiple comparison test (n=6). With calcium chloride, such significant increases in the expression of genes were not observed; in contrast, the expression levels of the versican and fibronectin genes significantly decreased compared to those with the control, which was an effect opposite to that of POs-Ca (R).

On the other hand, calcium chloride significantly increased the expression of VEGFB, compared to the control; in contrast, POs-Ca (R) significantly suppressed the expression of VEGFB.

Suppression of follicle dermal papilla cell apoptosis by POs-Ca (R) is demonstrated by the promotion of the expression of Wnt5a. Hair-follicle angiogenesis is demonstrated by the expression of VEGF. Promotion of hair matrix cell proliferation by POs-Ca (R) is demonstrated by the expression of FGF-7. Promotion of the activity of follicle dermal papilla cells by POs-Ca (R) is demonstrated by the promotion of the expression of ALPL and versican. Versican is an extracellular matrix specific to follicle dermal papilla cells. Promotion of anagen-phase hair follicles by POs-Ca (R) is demonstrated by the expression of tenascin C. Promotion of anagen-phase hair follicles by POs-Ca (R) is demonstrated by an increase in the expression of CSPG4. Fibronectin is an extracellular matrix that is extensively present, and is expected to promote follicle dermal papilla cells and the like when POs-Ca (R) is used. It is understood that through the upregulation of these genes, POs-Ca (R) causes follicle dermal papilla cells to demonstrate the function of hair-growth phase, resulting in the effect of promoting hair growth. Additionally, it is understood that POs-Ca (R) also has the effect of promoting hair growth in that it serves to suppress the expression of VEGFB, which is upregulated when general calcium agents are administered.

Example 4: Experiment for Comparison of POs-Ca (R) and Minoxidil

Next, in this example, an experiment similar to that of Example 3 was performed to compare POs-Ca (R) with the existing hair-growth agent, minoxidil.

(Materials and Method)

An experiment similar to that of Example 3 was performed, except that the procedure (2) was changed as follows:

(2) (a) Water (control), as well as (b) a 2.5% (w/v) aqueous solution of POs-Ca (R), (d) a 500 µM aqueous solution of minoxidil (final concentration: 50 µM), and (e) an aqueous solution of 2.5% (w/v) POs-Ca (R) and 500 µM minoxidil (final concentration of POs-Ca (R): 0.25%, final concentration of minoxidil: 50 µM), were prepared. Each of the solutions (a), (b), (d) and (e) was mixed with DMEM high glucose (Sigma, USA) at a ratio of 1:9. The minoxidil concentration was selected as a concentration that has been confirmed to exert an influence upon follicle dermal papilla cells, based on the results disclosed in Journal of Investigative Dermatology 117, 1594-1600 (2001).

(Results)

The results are shown in FIG. 3. The POs-Ca (R) treatment significantly enhanced the expression of the Wnt5a, ALPL, versican, fibronectin, VEGF, VEGFB, and FGF-7 genes, compared to the minoxidil treatment, in the Tukey multiple comparison test (N=6). While minoxidil is not fully certain in terms of mechanism of action, it is understood that the effects of POs-Ca (R) of the present invention differ from the effects of minoxidil in the following respects, and can complement the effects of minoxidil:

With respect to Wnt5a, a study of the presence of a significant difference compared to the control by the Tukey multiple comparison test (n=6) showed that there was a remarkable difference in that POs-Ca (R) demonstrated a significant effect, whereas minoxidil demonstrated little effect. It is thus understood that the agent of the present invention has the effect of suppressing follicle dermal papilla cell apoptosis that is not offered by minoxidil, and can complement the effects of minoxidil when used in combination with minoxidil.

With respect to VEGF, tenascin, and CSPG4, a study of the presence of a significant difference compared to the control by the Tukey multiple comparison test (n=6) showed that there was a remarkable difference in that POs-Ca (R) demonstrated a significant effect, whereas minoxidil demonstrated little effect. It is thus understood that the agent of the present invention is expected to have the effect of promoting hair follicles that is not offered by minoxidil, and can complement the effects of minoxidil when used in combination with minoxidil.

With respect to FGF-7, the effect of POs-Ca (R) was superior to that of minoxidil. It is thus understood that POs-Ca (R) is excellent in promoting the proliferation of hair matrix cells, and that the agent of the present invention is expected to have the effect of promoting the proliferation of hair matrix cells that is not offered by minoxidil, and can complement the effects of minoxidil when used in combination with minoxidil.

With respect to fibronectin and VEGFB, a study of the presence of a significant difference compared to the control by the Tukey multiple comparison test (n=6) showed that POs-Ca (R) demonstrated a statistically significant effect, whereas minoxidil did not. It is thus understood that POs-Ca (R) is expected to provide the hair-restoration or hair-growth effect that is not offered by minoxidil, and can complement the effects of minoxidil when used in combination with minoxidil.

Example 5: Test on the Combination of POs-Ca (R) and Adenosine

Next, in this example, a similar experiment to that in Example 3 was performed to compare POs-Ca (R) with the existing hair-restoration agent, adenosine.

(Materials and Method) An experiment similar to that of Example 3 was performed, except that the procedure (2) was changed as follows:

(2) (a) Water (control), as well as (b) a 2.5% (w/v) aqueous solution of POs-Ca (R), (d) a 500 µM aqueous solution of adenosine (final concentration: 50 µM), and (e) an aqueous solution of 2.5% (w/v) POs-Ca (R) and 500 µM adenosine (final concentration of POs-Ca (R): 0.25%, final concentration of adenosine: 50 µM), were prepared. Each of the solutions (a), (b), (d) and (e) was mixed with DMEM high glucose (Sigma, USA) at a ratio of 1:9. The adenosine concentration was selected as a concentration that has been confirmed to exert an influence upon follicle dermal papilla cells, based on the results disclosed in Journal of Investigative Dermatology 117, 1594-1600 (2001) and Journal of Investigative Dermatology 127, 1318-1325 (2007).

(Results)

The results are shown in FIGS. 4A and 4B. The treatment with the combination of POs-Ca (R) and adenosine synergistically augmented the expression levels of FGF-7 and CSPG4, compared to the treatment with POs-Ca (R) alone or adenosine alone. The expression of the Wnt5a, ALPL, versican, fibronectin, CSPG4, and tenascin genes was significantly enhanced, compared to that without treatment, in the Dunnett multiple comparison test (n=8). The expression levels of all the genes were such levels as achieved through the combination of the effects of both components, compared to those obtained with POs-Ca (R) alone or minoxidil alone. Adenosine has been indicated to exert an influence upon the expression of hair growth-related factors, by binding to MR and A2R, which are adenosine receptors on the cell membrane, and increasing the intracellular calcium concentration and cAMP (Journal of Investigative Dermatology 117, 1594-1600 (2001) and Journal of Investigative Dermatology 127, 1318-1325 (2007). It may be possible that POs-Ca (R) of the present invention contributes to an increase in the intracellular calcium ion concentration.

Example 6: Other Acidic Saccharide Alkaline Earth Metal Salts

Next, the expression rates of VEGF and FGF-7 were compared among other acidic saccharide alkaline earth metal salts in addition to POs-Ca (R), to demonstrate that other alkaline earth metal salts besides POs-Ca (R) can also be expected to similarly provide the effect of activating the proliferation of follicle dermal papilla cells, and the hair-restoration and hair-growth effects.

(Materials and Method)

(1) 500 μl of a special medium in which 2×10$^4$ cells/ml of follicle dermal papilla cells were suspended was dispensed into a type I collagen-coated 24-well cell culture plate (Corning), and cultured at a cell density of 5×10$^3$ cells/cm$^2$ at 37° C. for 72 hours.

(2) (a) Water (control), (b) a 2.5% (w/v) aqueous solution of POs-Ca (R), (c) a 0.457% (w/v) aqueous solution of CaCl$_2$, (d) a 3.23% (w/v) aqueous solution of G1P-Ca, (e) a 2.5% aqueous solution of a phosphorylated oligosaccharide sodium salt (POs-Na; Oji Cornstarch Co., Ltd.), (f) a 2.5% (w/v) aqueous solution of a phosphorylated oligosaccharide magnesium salt (POs-Mg; Oji Cornstarch Co., Ltd.), (g) an aqueous solution of 0.457% (w/v) CaCl$_2$·2.5% (w/v) maltotriose (Hayashibara), and (h) an aqueous solution of 1.19% (w/v) lactobionic acid sodium salt·0.457% (w/v) CaCl$_2$, were prepared. The solutions (b) to (h) had an equivalent calcium concentration.

(3) Each of the solutions (a) to (c) was mixed with DMEM high glucose (Sigma, USA) at a ratio of 1:9.

(4) Following the procedures (4) to (6) in Example 2, mRNA was extracted from the cells, cDNA was prepared, and then the expression levels of the VEGF, FGF-7, and GAPDH genes were quantified by quantitative PCR.

(7) Using GAPDH as a reference gene, a comparative analysis of expression levels was performed with the analysis software (Bio-Rad CFX Manager 3.0) included in CFX96Touch. The expression levels were calculated under the default conditions of the software.

(8) The quantitative PCR assay was repeated 4 times and the average value of the measurements was determined, and the value obtained by dividing the average value by the expression level of the control was defined as the expression rate.

(Results)

The following table shows a comparison of the expression rates of VEGF and FGF-7. With (c) calcium chloride, (g) the mixture of calcium chloride with maltotriose, which is an oligosaccharide not containing a phosphate group, and POs-Na, which is an alkali metal salt of phosphorylated oligosaccharides, the expression levels of the VEGF and FGF-7 genes were either comparable to or below the control. In contrast, (d) G1P-Ca, which is a calcium salt of a phosphorylated saccharide like POs-Ca (R), and (h) calcium lactobionate, which is a calcium salt of an acidic saccharide derivative, induced an increase in the expression levels of VEGF and FGF-7, as with POs-Ca (R). POs-Mg, which is an alkaline earth metal salt of phosphorylated oligosaccharides like POs-Ca (R), also had the effect of increasing the expression of both genes.

TABLE 3

Results of Example 6 (Relative values of the expression levels based on the control as 1 are shown)

| | Sample Name | VEGF | FGF7 |
|---|---|---|---|
| (b) | POs—Ca (R) | 1.38 | 1.82 |
| (c) | CaCl$_2$ | 0.80 | 1.02 |
| (d) | G1P—Ca | 1.46 | 1.10 |
| (e) | POs—Na | 0.70 | 1.08 |
| (f) | POs—Mg | 1.46 | 1.60 |
| (g) | CaCl$_2$ + Mal3 | 1.00 | 1.05 |
| (h) | Lactobio-Ca | 1.48 | 1.35 |

It is understood from the foregoing results that acidic saccharide alkaline earth metal salts in general, besides POs-Ca (R), have the effect of promoting the proliferation of follicle dermal papilla cells, the hair-restoration effect, and the hair-growth effect. In particular, POs-Mg and calcium lactobionate are expected to have an effect close to that of POs-Ca (R). However, a comparative experiment, though preliminary, showed that POs-Ca (R) was superior to POs-Mg and calcium lactobionate in the effect of promoting the proliferation of follicle dermal papilla cells, the hair-restoration effect, and the hair-growth effect, and thus, POs-Ca (R) is advantageous in a preferred embodiment.

Example 7: Variations in the Expression of Genes Induced by the Combination of POs-Ca (R) and Magnesium Next, in this example, variations in the expression of genes induced by the combination of POs-Ca (R) and magnesium were confirmed. Detail is given below.

(Materials and Method)

An experiment similar to that of Example 3 was performed, except that the procedures (1) and (2) were changed as follows:

With POs-Mg and MgCl$_2$·6H$_2$O having an equivalent amount of magnesium ions, the expression rates of VEGF, FGF7, and Wnt5a in follicle dermal papilla cells were compared to demonstrate the effect of the combination of acidic saccharides and magnesium.

(Materials and Method)

(1) 500 μl of a special medium in which 4×10$^4$ cells/ml of follicle dermal papilla cells were suspended was dispensed into a type I collagen-coated 24-well cell culture plate (Corning), and cultured at a cell density of 1×10$^4$ cells/cm$^2$ at 37° C. for 48 hours.

(2) (a) Water (control), as well as (b) a 2.5% (w/v) aqueous solution of POs-Mg, and (c) a 1.11% (w/v) aqueous solution of MgCl$_2$·6H$_2$O were prepared. Each of the solutions (a), (b), and (c) was mixed with DMEM high glucose (Sigma, USA) at a ratio of 1:9.

(Results)

Figure 5:
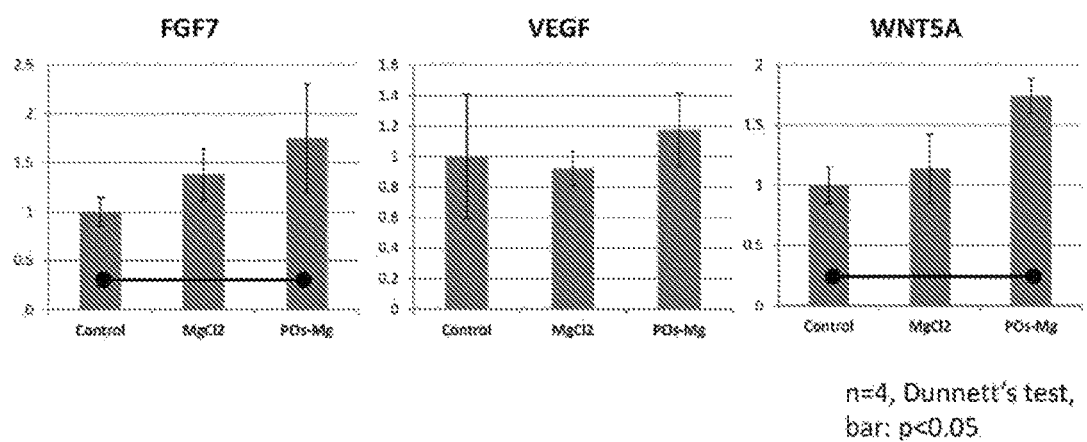
FIG. 5 shows the results of observation of variations in the expression of genes induced by the combination of POs-Ca (R) and magnesium. The experiment was performed by incubating a combination of 0.25% of POs-Ca (R) and 0.052% (final) of magnesium chloride in DMEM (serum-free) at 37° C. for 5 hours. Of FGF7, VEGF, and WNTSA (graphs from the left), the expression of FGF and WNTSA was significantly enhanced by POs-Mg, in Dunnett's test, $p<0.05$ ($p<0.05$ is shown by the lines each connecting black circles). It is believed that the phosphorylated saccharide achieved this effect by serving as a carrier for the metal ion.

With the phosphorylated oligosaccharide magnesium salt (POs-Mg), the expression of FGF7 and WNT5A increased with a significant difference, which was not observed with general magnesium. Although POs-Mg did not activate VEGF as much as POs-Ca (R) (FIG. 5), it still tended to increase the activation of VEGF. It is thus understood that the magnesium salt can also be used in the present invention.

Example 8: Variations in the Expression of Genes Induced by the Combination of POs-Ca (R) and General Hair-Restoration Components The effects of the addition of *Swertia japonica*, pantothenyl ethyl ether, tocopherol acetate, or glycyrrhizinate dipotassium, which are commonly used as hair-restoration agents in cosmetic products and quasi drugs, in combination with POs-Ca (R), compared to the effects of the addition of each of these components alone, were studied.

(Materials)

(1) Glycyrrhizinate dipotassium (for biochemical use) from Wako Pure Chemical Industries, Ltd. was diluted to 20% (w/v) with water, and sterilized by being passed through a 0.20-μm filter (Minisart, surfactant-free cellulose acetate, Sartorius Stedim Biotech, US) with a 10-ml syringe (Terumo Corporation), and the resulting product was diluted with sterilized water, as required, and used.

(2) (±)-α-Tocopherol acetate (first grade) from Wako Pure Chemical Industries, Ltd., as tocopherol acetate, and DL-pantothenyl ethyl ether from Santa Cruz Biotechnology, as pantothenyl ethyl ether, were each diluted 5-fold to 20% (v/v) with ethanol, and diluted with sterilized water, as required, and used.

(3) A water-ethanol solution of *Swertia japonica* extract from Senken Co., Ltd., as a 100% (v/v) extract, was diluted with sterilized water, as required, and used.

(Method)

(1) 500 μl of a special medium in which $2\times10^4$ cells/ml of follicle dermal papilla cells were suspended was dispensed into a type I collagen-coated 24-well cell culture plate (Corning), and cultured at a cell density of $5\times10^3$ cells/cm$^2$ at 37° C. for 96 hours, until the cells reached subconfluent.

(2) Solutions of the compositions shown in the following table were prepared, and each of the solutions was mixed with DMEM high glucose (Sigma, USA) at a ratio of 1:9.

TABLE 4

| | Without POs—Ca (R) | With POs—Ca (R) |
|---|---|---|
| Control | (a) Only Water | (b) 2.5% (w/v) POs—Ca (R) |
| 0.25% Glycyrrhizinate Dipotassium | (c) 2.5% (w/v) Glycyrrhizinate Dipotassium | (d) 2.5% (w/v) POs—Ca (R), 2.5% (w/v) Glycyrrhizinate Dipotassium |
| 1% Tocopherol Acetate | (e) 10% (v/v) Tocopherol Acetate | (f) 2.5% (w/v) POs—Ca (R), 10% (v/v) Tocopherol Acetate |
| 0.125% Pantothenyl Ethyl Ether | (g) 1.25% (v/v) Pantothenyl Ethyl Ether | (h) 2.5% (w/v) POs—Ca (R), 10% (v/v), 1.25% (w/v) Pantothenyl Ethyl Ether |
| 1% *Swertia japonica* Extract | (i) 10% *Swertia japonica* Extract (v/v) | (j) 2.5% (w/v) POs—Ca (R), 10% *Swertia japonica* Extract (v/v) |

(3) Two wells were used for culturing each of the DMEM solutions containing (a) to (i). The expression levels of FGF7 and VEGF were analyzed as in (3) to (8) of Example 3, and the average values of the two wells were compared.

(Results)

None of *Swertia japonica*, pantothenyl ethyl ether, tocopherol acetate, and glycyrrhizinate dipotassium, which are often used in hair-restoration agents for cosmetic products or quasi drugs, demonstrated a synergistic effect with POs-Ca (R) (FIG. 6).

Example 9: Preparations

Examples of agents for hair restoration will be described as examples of the present invention.

(1) Preparation 1

| POs—Ca (R) | 1.0 g |
|---|---|
| (Other Components) | |
| Polyvinyl Alcohol | 0.5 g |
| Glycyrrhizinate Dipotassium | 0.1 g |
| Distilled Water | Added to give a volume of 100 ml |
| Total | 100 ml |

Sources of the above-listed materials are as follows: POs-Ca (R) is available from Oji Cornstarch Co., Ltd., polyvinyl alcohol is available from Osaka Organic Chemical Industry Ltd. or BASF, and glycyrrhizinate dipotassium is available from Maruzen Pharmaceuticals Co., Ltd.

(2) Preparation 2

| POs—Ca (R) | 1.0 g |
|---|---|
| (Other Components) | |
| Ethanol | 5% |
| Polyvinyl Alcohol | 0.5 g |
| Glycyrrhizinate Dipotassium | 0.1 g |
| 1-Menthol | 0.3% |
| *Swertia japonica* Extract | 1.0% |
| (*Swertia japonica* Extract Liquid ET) | |
| Pantothenyl Ethyl Ether | 1% |
| Ginseng Extract | 1.0% |
| Tocopherol Acetate | 100 mg |
| Distilled Water | Added to give a volume of 100 ml |
| Total | 100 ml |

Sources of the above-listed materials are as follows: POs-Ca (R) is available from Oji Cornstarch Co., Ltd., pantothenyl ethyl ether is available from DSM Nutrition Japan K.K., tocopherol acetate is available from Iwase Cosfa Co., Ltd., and the other materials are available from Maruzen Pharmaceuticals Co., Ltd.

While the present invention has been illustrated above using preferred embodiments of the present invention, it is to be understood that the scope of the present invention should be interpreted based on the scope of the claims only. It is to be understood that the patents, patent applications, and documents cited herein should be incorporated herein by reference as if the contents per se were specifically described herein. The present application claims priority from Japanese Patent Application No. 2014-235352, of which contents are incorporated herein by reference in its entirety as if to entirely form a part of the present application.

INDUSTRIAL APPLICABILITY

Cosmetic products (such as agents for hair restoration, shampoos, and hair styling products), pharmaceutical products, agents for hair restoration for pets, and phosphorylated saccharide calcium per se for hair-restoration purposes can be provided.

Sequence Listing Free Text

SEQ ID NO: 1: fibronectin primer 1 (forward):
CCCATCAGCAGGAACACCTT

SEQ ID NO: 2: fibronectin primer 2 (reverse):
GGCTCACTGCAAAGACTTTGAA

SEQ ID NO: 3: CSPG4 primer 1 (forward):
AGCTAGCCAGGACTGATGGA

SEQ ID NO: 4: CSPG4 primer 2 (reverse):
CAGCCTAACCTGCTCCAAAG

SEQ ID NO: 5: tenascin C primer 1 (forward):
AGGGACCACTGGGTGAGAGA

SEQ ID NO: 6: tenascin C primer 2 (reverse):
GGGCTGGTTGTATTGATGCTTT

SEQ ID NO: 7: versican primer 1 (forward):
CAAGCATCCTGTCTCACGAA

SEQ ID NO: 8: versican primer 2 (reverse):
CAACGGAAGTCATGCTCAAA

SEQ ID NO: 9: ALPL primer 1 (forward):
GACCCTTGACCCCCACAAT

SEQ ID NO: 10: ALPL primer 2 (reverse):
GCTCGACTGCATGTCCCCT

SEQ ID NO: 11: Wnt5a primer 1 (forward):
AGGGCTCCTACGAGAGTGCT

SEQ ID NO: 12: Wnt5a primer 2 (reverse):
GACACCCCATGGCACTTG

SEQ ID NO: 13: VEGF primer 1 (forward):
CTACCTCCACCATGCCAAGT

SEQ ID NO: 14: VEGF primer 2 (reverse):
AGCTGCGCTGATAGACATCC

SEQ ID NO: 15: VEGFB primer 1 (forward):
GCAGATCCTCATGATCCGGT

SEQ ID NO: 16: VEGFB primer 2 (reverse):
GGCTTCACAGCACTGTCCTT

SEQ ID NO: 17: FGF-7 primer 1 (forward):
TGTCGAACACAGTGGTACCTG

SEQ ID NO: 18: FGF-7 primer 2 (reverse):
CCCTTTGATTGCCACAATTC

SEQ ID NO: 19: PGK1 primer 1 (forward):
AGGGAAAAGATGCTTCTGGG

SEQ ID NO: 20: PGK1 primer 2 (reverse):
AAGTGAAGCTCGGAAAGCTTCTAT

SEQ ID NO: 21: GAPDH primer 1 (forward):
ACAGTCAGCCGCATCTTCTT

SEQ ID NO: 22: GAPDH primer 2 (reverse):
ACGACCAAATCCGTTGACTC

---

The invention claimed is:

1. A method for activating proliferation of follicle dermal papilla cells comprising the step of administering a composition comprising an effective amount of a combination of an alkaline earth metal and an acidic saccharide as well as a pharmacologically acceptable carrier to a subject in need of the activation of proliferation, wherein the combination of the alkaline earth metal and the acidic saccharide is selected from the group consisting of
   i) a phosphorylated oligosaccharide alkaline earth metal salt;
   ii) a combination of a phosphorylated oligosaccharide or alkali metal salt thereof, and an alkaline earth metal salt;
   iii) an alkaline earth metal salt of glucose-1-phosphate;
   iv) a combination of a glucose-1-phosphate or alkali metal salt thereof, and an alkaline earth metal salt;
   v) an alkaline earth metal salt of lactobionic acid; and
   vi) a combination of lactobionic acid or alkali metal salt thereof, and an alkaline earth metal salt;
   wherein the composition further comprises adenosine.

2. The method according to claim 1, wherein the combination of an alkaline earth metal and an acidic saccharide is selected from the group consisting of:
   i) a phosphorylated oligosaccharide alkaline earth metal salt;
   ii) a combination of a phosphorylated oligosaccharide or alkali metal salt thereof, and an alkaline earth metal salt;
   iii) an alkaline earth metal salt of glucose-1-phosphate; and
   iv) a combination of a glucose-1-phosphate or alkali metal salt thereof, and an alkaline earth metal salt.

3. The method according to claim 1, wherein the alkaline earth metal is calcium or magnesium.

4. The method according to claim 1, wherein the alkaline earth metal is calcium.

5. The method according to claim 1, wherein the combination of an alkaline earth metal and an acidic saccharide is lactobionic acid calcium salt, glucose-1-phosphate calcium salt (G1P-Ca), a phosphorylated oligosaccharide calcium salt (POs-Ca (R)), or a phosphorylated oligosaccharide magnesium salt (POs-Mg).

6. The method according to claim 1, wherein the combination of an alkaline earth metal and an acidic saccharide is a phosphorylated oligosaccharide calcium salt (POs-Ca (R)), or a combination of a phosphorylated oligosaccharide or alkali metal salt thereof, and a calcium salt.

7. The method according to claim 1, wherein the combination of an alkaline earth metal and an acidic saccharide is a phosphorylated oligosaccharide calcium salt (POs-Ca (R)).

8. The method according to claim 1, wherein proliferation of hair matrix cells is also promoted by administering said composition.

9. The method according to claim 1, wherein proliferation of hair follicles is also promoted by administering the composition.

10. The method according to claim 1, wherein proliferation of hair matrix cells and hair follicles is also promoted by administering said composition.

* * * * *